US011419894B2

(12) United States Patent
Poznansky et al.

(10) Patent No.: US 11,419,894 B2
(45) Date of Patent: Aug. 23, 2022

(54) MODIFIED NATURAL KILLER CELLS FOR THE TREATMENT OF CANCER

(71) Applicant: The General Hospital Corporation, Boston, MA (US)

(72) Inventors: Mark C. Poznansky, Newton Center, MA (US); Patrick Reeves, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 491 days.

(21) Appl. No.: 16/332,981

(22) PCT Filed: Sep. 15, 2017

(86) PCT No.: PCT/US2017/051787
§ 371 (c)(1),
(2) Date: Mar. 13, 2019

(87) PCT Pub. No.: WO2018/053270
PCT Pub. Date: Mar. 22, 2018

(65) Prior Publication Data
US 2019/0269729 A1    Sep. 5, 2019

Related U.S. Application Data

(60) Provisional application No. 62/396,042, filed on Sep. 16, 2016.

(51) Int. Cl.
| A61K 35/17 | (2015.01) |
| A61P 35/00 | (2006.01) |
| A61K 35/76 | (2015.01) |
| A61K 38/17 | (2006.01) |
| C07K 14/55 | (2006.01) |
| C07K 14/705 | (2006.01) |
| A61K 45/06 | (2006.01) |
| C07K 14/735 | (2006.01) |

(52) U.S. Cl.
CPC .............. *A61K 35/17* (2013.01); *A61K 35/76* (2013.01); *A61K 38/17* (2013.01); *A61K 45/06* (2013.01); *A61P 35/00* (2018.01); *C07K 14/55* (2013.01); *C07K 14/705* (2013.01); *C07K 14/70535* (2013.01)

(58) Field of Classification Search
None
See application file for complete search history.

(56) References Cited

U.S. PATENT DOCUMENTS

| 5,514,555 A | 5/1996 | Springer et al. |
| 5,583,131 A | 12/1996 | Bridger et al. |
| 8,034,332 B2 | 10/2011 | Klingemann |
| 8,313,943 B2* | 11/2012 | Campbell ............. C07K 16/28 435/325 |
| 10,973,852 B2* | 4/2021 | Soon-Shiong ..... A61K 38/1793 |
| 2008/0300165 A1 | 12/2008 | Poznansky et al. |
| 2015/0110757 A1 | 4/2015 | Holmes et al. |
| 2016/0199470 A1 | 7/2016 | Chavan et al. |

FOREIGN PATENT DOCUMENTS

WO    2017/083441    5/2017

OTHER PUBLICATIONS

Szmania et al. "Ex Vivo Expanded Natural Killer Cells Demonstrate Robust Proliferation In Vivo 1, 11—In High-Risk Relapsed Multiple Myeloma Patients," J Immunother, Jan. 30, 2015 (Jan. 30, 2015), vol. 38, Iss. 1, pp. 24-36. (Year: 2015).*
Szmania et al. "Ex Vivo Expanded Natural Killer Cells Demonstrate Robust Proliferation In Vivo 1, 11—In High-Risk Relapsed Multiple Myeloma Patients," J Immunother, Jan. 30, 2015 (Jan. 8, 2015), vol. 38, Iss. 1, pp. 24-36. (Year: 2015).*
Sierra et al. (PNAS. Sep. 11, 2007; 104(37): 14759-14764). (Year: 2007).*
Martín et al. (Cell Press. Trends in Molecular Medicine, Jan. 2013, vol. 19, No. 1; pp. 12-22) (Year: 2013).*
International Preliminary Report on Patentability corresponding to International Application No. PCT/US2017/051787 dated Mar. 28, 2019.
International Search Report and Written Opinion corresponding to International Application No. PCT/US2017/051787 dated Dec. 15, 2017.
Klingemann et al. "Natural Killer Cells for Immunotherapy—Advantages of the NK-92 Cell Line over Blood NK Cells", Frontiers in Immunology 7(Art. 91):1-7 (2016).
Szmania et al., "Ex Vivo Expanded Natural Killer Cells Demonstrate Robust Proliferation In Vivo In High-Risk Relapsed Multiple Myeloma Patients", J. Immunother. 38(1):24-36 (2015).
Eshhar et al., "Specific activation and targeting of cytotoxic lymphocytes through chimeric single chains consisting of antibody-binding domains and the γ or ζ subunits of the immunoglobulin and T-cell receptors," Proc. Natl. Acad. Sci., 1993, 90(2):720-724.
Gong et al., "Characterization of a human cell line (NK-92) with phenotypical and functional characteristics of activated natural killer cells," Leukemia, Apr. 1994, 8(4):652-658.

(Continued)

*Primary Examiner* — Scott Long
(74) *Attorney, Agent, or Firm* — Fish & Richardson P.C.

(57) ABSTRACT

This invention is directed to the treatment of cancers, e.g., inflammatory breast cancer, with NK (natural killer) cells wherein the cells are modified ex vivo such that their ability to overcome the chemorepellant effect of a tumor is enhanced. The cells may be genetically modified ex vivo and/or modified by contacting the cells ex vivo with an anti-chemorepellant agent. This invention also provides ex vivo modified NK cells, which are modified such that they express no or substantially no CXCR4 on their cell surface, or express CXCR7, or express a chimeric antigen receptor, or combinations thereof. The invention also relates to methods for treating a patient having a tumor, e.g., inflammatory breast cancer, by administering the modified NK cells, with or without treatment with other conventional anticancer treatments, e.g., chemotherapy, radiotherapy, viral therapies, hormonal therapies, as well as other immunotherapies and anti-chemorepellant therapies.

20 Claims, No Drawings

(56) References Cited

OTHER PUBLICATIONS

Liu et al., "Chemokine Receptor CXCR7 Is a Functional Receptor for CXCL12 in Brain Endothelial Cells," PlosONE, Aug. 2014, 9(8):e103938, 9 pages.

Uto-Konomi et al., "CXCR7 agonists inhibit the function of CXCL12 by down-regulation of CXCR4," Biochem Biophys Res Commun., 2013, 431(4):772-776.

Wurth et al., "CXCL12 modulation of CXCR4 and CXCR7 activity in human glioblastoma stem-like cells and regulation of the tumor microenvironment," Front. Cell. Neurosci., 2014, 8:144, 19 pages.

Zhao et al., "CXCR4 over-expression and survival in cancer: A system review and meta-analysis," Oncotarget, 2015, 6(7):5022-5040.

* cited by examiner

MODIFIED NATURAL KILLER CELLS FOR THE TREATMENT OF CANCER

STATEMENT OF PRIORITY

This application is a 35 U.S.C. § 371 national phase application of PCT Application PCT/US2017/051787 filed Sep. 15, 2017, which claims the benefit of U.S. Provisional Application Ser. No. 62/396,042, filed Sep. 16, 2016, the entire contents of each of which are incorporated by reference herein in its entirety.

FIELD OF THE INVENTION

This invention is directed to the treatment of cancers, e.g., inflammatory breast cancer, with NK (natural killer) cells wherein the cells are modified ex vivo such that their ability to overcome the chemorepellant effect of a tumor is enhanced. The cells may be genetically modified ex vivo and/or modified by contacting the cells ex vivo with an anti-chemorepellant agent. This invention also provides ex vivo modified NK cells, which are modified such that they express no or substantially no CXCR4 on their cell surface, or express CXCR7, or express a chimeric antigen receptor, or combinations thereof. The invention also relates to methods for treating a patient having a tumor, e.g., inflammatory breast cancer, by administering the modified NK cells, with or without treatment with other conventional anticancer treatments, e.g., chemotherapy, radiotherapy, viral therapies, hormonal therapies, as well as other immunotherapies and anti-chemorepellant therapies.

BACKGROUND OF THE INVENTION

Cell movement in response to specific stimuli is observed in prokaryotes and eukaryotes. Cell movement seen in these organisms has been classified into three types: chemotaxis, or the movement of cells along a gradient towards an increasing concentration of a chemical; negative chemotaxis, which has been defined as the movement down a gradient of a chemical stimulus; and chemokinesis, or the increased random movement of cells induced by a chemical agent.

Chemotaxis and chemokinesis occur in mammalian cells in response to the class of proteins, called chemokines. Additionally, chemorepellant, or fugetactic, activity has been observed in mammalian cells. For example, some tumor cells secrete concentrations of chemokines that are sufficient to repel immune cells from the site of a tumor, thereby reducing the immune system's ability to target and eradicate the tumor. Metastasizing cancer cells may use a similar mechanism to evade the immune system. Repulsion of tumor antigen specific T-cells, e.g., from a tumor expressing high levels of CXCL12 or interleukin 8 (IL-8), allows the tumor cells to evade immune control.

Chemokines are crucial autocrine and paracrine players in tumor development. In particular, CXCL12 (also known as SDF-1), through its receptors CXCR4 and CXCR7, affects tumor progression by controlling cancer cell survival, proliferation and migration, and, indirectly, via angiogenesis or recruiting immune cells (Wurth, R. et al. (2014), Frontiers in Cellular Neuroscience, 8:144). CXCL12 is also known to be important in hematopoietic stem cell homing to the bone marrow and in hematopoietic stem cell quiescence.

CXCR4 is a protein that in humans is encoded by the CXCR4 gene. CXCR4 is expressed by multiple normal cells as well as on tumors. CXCR4 is an alpha-chemokine receptor specific for stromal-derived-factor-1 (SDF-1, also known as CXCL12), a molecule endowed with potent chemotactic activity for lymphocytes. CXCL12, a ligand for CXCR4, is known to be important in hematopoietic stem cell homing to the bone marrow and in hematopoietic stem cell quiescence. While CXCR4 expression is low or absent in many healthy tissues, it has been demonstrated that CXCR4 is highly expressed in various different tumor types and has been considered the most widely expressed chemokine receptor in cancer. Overexpression of CXCR4 has also been shown to be associated with poorer prognosis irrespective of cancer type (Zhao et al, (2015) Oncotarget 6(7):5022-5040). Expression of this receptor in cancer cells has been linked to metastasis to tissues containing a high concentration of CXCL12, such as lungs, liver and bone marrow.

As many as 85% of solid tumors and leukemias express CXCL12 at a level sufficient to have chemorepellant effects, e.g., repulsion of immune cells from the tumor. Cancers that frequently express CXCL12 at such levels include, but are not limited to, glioma, prostate cancer, lung cancer, breast cancer, e.g., inflammatory breast cancer, pancreatic cancer, ovarian cancer, head and neck cancer, anal cancer, gastric cancer, esophageal cancer, and leukemia.

Inflammatory breast cancer is a rare and very aggressive disease in which cancer cells block lymph vessels in the skin of the breast. This type of breast cancer is called "inflammatory" because the breast often looks swollen and red, or inflamed. Inflammatory breast cancer is rare, accounting for 1 to 5 percent of all breast cancers diagnosed in the United States. Most inflammatory breast cancers are invasive ductal carcinomas, which means they developed from cells that line the milk ducts of the breast and then spread beyond the ducts. Inflammatory breast cancer progresses rapidly, often in a matter of weeks or months. At diagnosis, inflammatory breast cancer is either stage III or IV disease, depending on whether cancer cells have spread only to nearby lymph nodes or to other tissues as well. Inflammatory breast cancer is generally treated first with systemic chemotherapy to help shrink the tumor, then with surgery to remove the tumor, followed by radiation therapy. This approach to treatment is called a multimodal approach. Studies have found that women with inflammatory breast cancer who are treated with a multimodal approach have better responses to therapy and longer survival. Because inflammatory breast cancer usually develops quickly and spreads aggressively to other parts of the body, women diagnosed with this disease, in general, do not survive as long as women diagnosed with other types of breast cancer. See, www.cancer.gov/types/breast/ibc-fact-sheet.

Anti-chemorepellant agents inhibit the chemorepellant activity of tumor cells and allow the patient's immune system to target the tumor. Anti-chemorepellant agents and the systemic delivery of anti-chemorepellant agents are known in the art (see, for example, U.S. Patent Application Publication No. 2008/0300165, incorporated herein by reference in its entirety). However, the delivery of anti-chemorepellant agents as heretofore described will likely result in a portion of the anti-chemorepellant agent binding to the CXCR4 receptors on a tumor or other sites thus making the effective concentration of the anti-chemorepellant agent that binds to immune cells unpredictable.

Furthermore, immune cell therapy (i.e., infusion of autologous, allogenic, or immortalized immune cells into a patient) has shown that the infused immune cells may get "stuck" in particular tissues, leading to eradication of the infused immune cells before they are able to reach the target cancer cells. In particular, infused natural killer (NK) cells may preferentially congregate in the lung, spleen, and/or liver.

Accordingly, there remains a need for compositions that target cancers, particularly inflammatory breast cancer, with increased specificity and efficiency and methods that effectively and efficiently kill tumors and/or metastasizing cancer cells.

SUMMARY OF THE INVENTION

Described herein are ex vivo modified NK cells, and compositions comprising such cells. In some embodiments, the NK cells are NK-92 cells, NK-YS cells, KHYG-1 cells, NKL cells, NKG cells, SNK-6 cells, or IMC-1 cells, or a genetically modified cell line derived therefrom. In some embodiments the NK cells are not NK-92 cells, NK-YS cells, KHYG-1 cells, NKL cells, NKG cells, SNK-6 cells, or IMC-1 cells. In some embodiments, the modified NK cells are generated by genetic editing using a nuclease (e.g., Zinc finger nucleases (ZFNs), Transcription Activator-Like Effector Nucleases (TALENs), the CRISPR/Cas system, or engineered meganuclease and re-engineered homing endonucleases). In some embodiments the NK-92 cells are genetically modified to express IL-2 or CD-16 (see e.g., U.S. Pat. Nos. 8,313,943 and 8,034,332, incorporated in their entirety by reference).

Also described herein are methods for treating a patient in need thereof by administering modified NK cells or pharmaceutical compositions comprising the modified cells. A patient in need thereof is, e.g., a patient having a cancer or tumor, particularly a cancer or tumor which expresses or overexpresses CXCL12. The cancer may be a breast cancer, e.g., an inflammatory breast cancer.

In one embodiment, the ex vivo modified NK cells described herein express no or substantially no CXCR4 on the cell surface. The expression of CXCR4 in the modified NK cells is reduced directly or indirectly such that the level of CXCR4 on the surface of the modified cell is eliminated, or reduced to a level such that the modified NK cells evade the chemorepellant effect of a chemokine-expressing cancer, e.g., a CXCL12-expressing cancer. In an aspect of this invention, the modified NK cells, described herein are ex vivo modified to express an altered CXCR4 protein on the cell surface, such that CXCL12 fails to bind to the altered CXCR4 protein, or binds at a reduced level. The modified cells thereby target the tumor more efficiently than unmodified NK cells, and effectively inhibit the growth, progression and/or metastasis of the cancer or tumor. Without wishing to be bound by theory, having no or substantially no CXCR4 on the surface the modified cells enhances the ability of such cells to evade the chemorepellant effect of a chemokine expressing cancer, e.g., a CXCL12-expressing cancer, and thereby attack the cancer.

In an aspect of this invention, the ex vivo modified NK cells may be genetically modified to express or overexpress CXCR7 (also known as RDC1), another receptor for CXCL12 (Liu et al. (August 2014) PlosONE 9(8) e103938: 1-9) and/or a tumor cell homing receptor on the surface of the cell. CXCR7 is thought to form homodimers, or heterodimers with CXCR4, and is believed to sequester the chemokine CXCL12 (Uto-Komomi, S. et al., (2013) Biochem Biophys Res Commun. 431(4): 772-6)) (see e.g., Human RefSeq (mRNA) NM_001047841; RefSeq (protein) NP_064707; Location (UCSC) Chr 2: 236.57-236.58 Mb). The sequence of CXCR7 is known and vectors comprising the CXCR7 coding sequence are commercially available.

The tumor cell homing receptor may be, e.g., a chimeric antigen receptor ("CAR"), an Fc receptor, or combinations thereof. The CAR may target a cancer-associated antigen. The cancer associated antigen may be, e.g., folate receptor-α, CAIX, CD19, CD20, CD30, CD33, CEA, EGP-2, erb-B2, erb-B 2,3,4, FBP, GD2, GD3, Her2/neu, IL-13R-a2, k-light chain, LeY, MAGE-A1, mesothelin, or PSMA. In some embodiments the modified NK cells express an endogenous tumor cell homing receptor that is not CXCR4.

The modified NK cells, described herein expressing substantially no CXCR4 may have less than about 50%, 25%, 15%, 10%, 5%, 1% or less of the amount of CXCR4 receptors on their cell surface as compared to the average number of CXCR4 receptors on a control cell, e.g., the NK cells, prior to modification of the CXCR4 expression levels.

Another embodiment of this invention is an ex vivo population of immune cells comprising modified NK cells having no or substantially no CXCR4 receptors on the surface of the cells.

The population of modified NK cells described herein may further comprise immune cells, including NK cells genetically modified to express a tumor cell homing receptor on the surface of the immune cell. The tumor cell homing receptor may be a CAR, an Fc receptor, or combinations thereof. The CAR may target a cancer-associated antigen. The cancer associated antigen may be e.g., folate receptor-α, CAIX, CD19, CD20, CD30, CD33, CEA, EGP-2, erb-B2, erb-B 2,3,4, FBP, GD2, GD3, Her2/neu, IL-13R-a2, k-light chain, LeY, MAGE-A1, mesothelin, or PSMA. In an embodiment of this invention at least a portion of the modified NK cells in the population express an endogenous tumor cell homing receptor that is not CXCR4, e.g., at least about 10%, 20%, 30%, 40%, 50%, 60%, 70%, 80%, or 90% or more of the cells.

In an aspect of this invention the modified NK cells have 50% or less of the amount of CXCR4 receptors on their cell surface as compared to the average number of CXCR4 receptors on unmodified NK cells of the same type.

The methods of administering modified NK cells of this invention to a subject as described herein involve the use of pharmaceutical compositions comprising the modified NK cells. The compositions may further comprise an anticancer agent. Pharmaceutical compositions contain a physiologically tolerable carrier together with the modified NK cells or compositions comprising the modified NK cells.

Also an aspect of this invention are pharmaceutical compositions comprising the modified NK cells described herein. In general, the modified NK cells described herein are administered as a suspension with a pharmaceutically acceptable carrier. The compositions may further comprise an anticancer agent.

An aspect of this invention is a method of making modified NK cells ex vivo such that they express no or substantially no CXCR4. Such NK cells may be ex vivo genetically modified using any suitable genetic editing technologies, e.g., ZFN, TALEN, and CRISPR. The CXCR4 gene may be deleted in whole or part or may be modified such that the modified CXCR4 gene encodes a mutant CXCR4 protein having altered stability or binding to CXCL12, intracellular trafficking, recycling and/or localization to the membrane.

An aspect of this invention is a method of making a modified NK cell or a population of modified NK cells wherein the cells are engineered such that the CXCR4 gene is modified by a deletion, an insertion, or a substitution resulting in no or reduced expression of a CXCR4 protein or production of a CXCR4 mutant protein.

In an aspect of this invention the mutant protein produced by such modified CXCR4 gene has a reduced stability and/or binding activity such that the altered protein has no or substantially reduced binding to CXCL12.

In an aspect of this invention, the mutant protein produced by a modified CXCR4 gene has no or reduced membrane localization or intracellular trafficking and/or recycling thereby reducing the sensitivity of the modified NK cells to the chemorepellant effect of a chemokine-expressing tumor, e.g., a CXCL12-expressing tumor.

It is contemplated that the modifications of the CXCR4 gene may be in the regulatory, coding, or non-coding regions of the CXCR4 gene provided such modification result in no or reduced expression of a CXCR4 protein or production of a CXCR4 mutant protein. The CXCR4 mutants useful in this invention have a reduced stability and/or binding activity such that the altered protein has no or substantially reduced binding of CXCL12, or no or reduced membrane localization and/or trafficking and/or recycling. One of skill in the art can readily determine nucleic acid sequence modifications that will result in amino acid substitution that would be expected to alter the structure and therefore the stability and/or activity of a protein such as CXCR4, e.g., non-conservative amino acid substitutions, e.g., substituting a proline for a cysteine. Other non-limiting examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

The expression of CXCR4 in the modified NK cells can be reduced indirectly by reducing the level of a molecule that induces CXCR4 expression.

Another aspect of this invention is a method for generating a modified NK cell expressing no or substantially no CXCR4 on its cell surface, the method comprising (a) obtaining an NK cell population; (b) modifying the NK cell population wherein at least a portion of said modified NK cells expresses no or substantially no CXCR4 on the cell surface, or express a mutant CXCR4 having no or reduced binding to CXCL12 or reduced stability, membrane localization and/or recycling activity, e.g., at least about 10%, 20%, 30%, 40%, 50%, 60%, 70%, 80%, or 90% or more of the cells. Such ex vivo modified NK cells, may be further modified to express another molecule, e.g., CXCR7, IL-2, CD16, or a CAR.

In an aspect of this invention, a population of NK cells comprising modified NK cells expressing no or substantially no CXCR4 on its surface, which may be further modified to express a CXCR7, CD16, CAR or IL-2, may be further contacted with an anti-chemorepellant agent to provide a composition for the efficient and effective treatment of cancers.

Another aspect of this invention is a population of NK cells comprising NK cells having an anti-chemorepellant agent bound to individual NK cells. In one embodiment, the anti-chemorepellant agent is bound to the cells through a receptor on the cell surface. In one embodiment, the receptor is CXCR4. In one embodiment, the receptor is CXCR7. In one embodiment, varying amounts of the anti-chemorepellant agent are bound to individual NK cells. In one embodiment, at least a portion of the receptors on each cell are occupied by the agent. In one embodiment, the anti-chemorepellant agent is bound to individual NK cells. In one embodiment, the NK cells are not modified to express no or substantially no CXCR4 on the cell surface.

Anti-chemorepellant agents may include, without limitation, molecules that inhibit expression of CXCL12 or CXCR4 or CXCR7 (e.g., antisense or siRNA molecules), molecules that bind to CXCL12 or CXCR4 or CXCR7 and inhibit their function (e.g., antibodies or aptamers), molecules that inhibit dimerization of CXCL12 or CXCR4 or CXCR7, and antagonists of CXCR4 or CXCR7. In one embodiment, the inhibitor of CXCL12 signaling is a CXCR4 antagonist. In one embodiment, the anti-chemorepellant agent is AMD3100 or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, TN14003, TAK-779, AK602, SCH-351125, tannic acid, NSC 651016, thalidomide, GF 109230X, an antibody that interferes with dimerization of a chemorepellant chemokine, such as CXCL12, or an antibody that interferes with dimerization of a receptor for a chemorepellant chemokine, such as CXCR4 or CXCR7. In one embodiment, the anti-chemorepellant agent is AMD3100 (1,1'-[1,4-phenylenebis(methylene)]bis[1,4,8,11-tetraazacyclotetradecane]; plerixafor). AMD3100 is described in U.S. Pat. No. 5,583,131, which is incorporated by reference herein in its entirety. In one embodiment, the anti-chemorepellant agent is a CXCR7 antagonist. The CXCR7 antagonist can be but is not limited to CCX771, CCX754, or an antibody that interferes with the dimerization of CXCR7. In certain embodiments, the anti-chemorepellant agent is not an antibody. In certain embodiments, the anti-chemorepellant agent is not a heparinoid. In certain embodiments, the anti-chemorepellant agent is not a peptide.

Also included herein is a method for treating a patient having a tumor which expresses CXCL12, in particular high levels of CXCL12, wherein said patient is administered an effective amount of modified NK cells or compositions comprising the modified NK cells described herein. High levels of CXCL12 are levels of CXCL12 that exert a chemorepellant effect on immune cells, e.g., greater than about 100 nM.

The modified NK cells of this invention may be administered by any method routinely used in the art. For example the modified NK cells may be administered systemically to a patient in need thereof, or the modified NK cells may be administered directly to the tumor or tumor microenvironment, or combinations thereof.

In an aspect of this invention, the modified NK cells may also be administered in combination with any conventional anti-cancer therapy or agent, e.g., a chemotherapy, radiotherapy, hormonal therapy, viral therapy, immunotherapy, anti-chemorepellant therapy and combinations thereof. In an aspect of this invention, the modified NK cells are administered in combination with an anti-chemorepellant therapy or agent. The modified NK cells may be administered before, after, or concurrently with the anticancer and anti-chemorepellant therapy or agent

DETAILED DESCRIPTION

After reading this description, it will become apparent to one skilled in the art how to implement the invention in various alternative embodiments and alternative applications. However, not all embodiments of the present invention are described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Definitions

Unless defined otherwise, all technical and scientific terms used herein have the same meaning as commonly understood by one of ordinary skill in the art to which this invention belongs.

In accordance with this detailed description, the following abbreviations and definitions apply. It must be noted that as used herein, the singular forms "a," "and," and "the" include plural referents unless the context clearly dictates otherwise. Thus, for example, reference to "the dosage" includes reference to one or more dosages and equivalents thereof known to those skilled in the art.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

"Administration," "administering" or the like as used herein encompasses all suitable means of providing a substance to a patient. Common routes include intramuscular, intravenous, intra-arterial, intrathecal, oral, rectal, subcutaneous, sublingual, topical, transmucosal, transdermal, vaginal, via catheter, via implant etc. In some embodiments, a composition is administered near or directly to the tumor, such as by direct injection into the tumor blood vessel or injection into a blood vessel leading to the tumor or injection into the tumor such as when the tumor is a tumor of the blood. A cell composition can be administered by any appropriate route which results in effective treatment in the subject, i.e., administration results in delivery to a desired location in the subject where at least a portion of the composition delivered, i.e., at least $1 \times 10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. For the delivery of cells, administration by injection or infusion is generally preferred.

"Allogeneic" as used herein refers to cells obtained from one or more different donors of the same species, where the genes at one or more loci are not identical. In other embodiments of this aspect, the immune cells are "autologous cells," that is, the immune cells are obtained or isolated from a subject and administered to the same subject, i.e., the donor and recipient are the same.

"Antibodies" as used herein include polyclonal, monoclonal, single chain, chimeric, humanized and human antibodies, prepared according to conventional methodology. Table 1 depicts a non-limiting list of antibodies that are known and used for the treatment of cancer.

TABLE 1

Therapeutic monoclonal antibodies approved or in review in the European Union or the United States

| International non-proprietary name | Trade name | Target; Format | Indication first approved or reviewed | First EU approval year | First US approval year |
| --- | --- | --- | --- | --- | --- |
| Ado-trastuzumab emtansine | Kadcyla | HER2; humanized IgG1; immunoconjugate | Breast cancer | 2013 | 2013 |
| Alemtuzumab | MabCampath, Campath-1H; Lemtrada | CD52; Humanized IgG1 | Chronic myeloid leukemia#; multiple sclerosis | 2001#; 2013 | 2001#; 2014 |
| Bevacizumab | Avastin | VEGF; Humanized IgG1 | Colorectal cancer | 2005 | 2004 |
| Blinatumomab | Blincyto | CD19, CD3; Murine bispecific tandem scFv | Acute lymphoblastic leukemia | In review | 2014 |
| Brentuximab vedotin | Adcetris | CD30; Chimeric IgG1; immunoconjugate | Hodgkin lymphoma, systemic anaplastic large cell lymphoma | 2012 | 2011 |
| Cetuximab | Erbitux | EGFR; Chimeric IgG1 | Colorectal cancer | 2004 | 2004 |
| Dinutuximab | Unituxin | GD2; Chimeric IgG1 | Neuroblastoma | EC decision pending | 2015 |

TABLE 1-continued

Therapeutic monoclonal antibodies approved or in review in the European Union or the United States

| International non-proprietary name | Trade name | Target; Format | Indication first approved or reviewed | First EU approval year | First US approval year |
|---|---|---|---|---|---|
| Gemtuzumab ozogamicin | Mylotarg | CD33; Humanized IgG4 | Acute myeloid leukemia | NA | 2000# |
| Ibritumomab tiuxetan | Zevalin | CD20; Murine IgG1 | Non-Hodgkin lymphoma | 2004 | 2002 |
| Infliximab | Remicade | TNF; Chimeric IgG1 | Crohn disease | 1999 | 1998 |
| Ipilimumab | Yervoy | CTLA-4; Human IgG1 | Metastatic melanoma | 2011 | 2011 |
| Natalizumab | Tysabri | a4 integrin; Humanized IgG4 | Multiple sclerosis | 2006 | 2004 |
| Necitumumab | (Pending) | EGFR; Human IgG1 | Non-small cell lung cancer | In review | In review |
| Nivolumab | Opdivo | PD1; Human IgG4 | Melanoma, non-small cell lung cancer | EC decision pending | 2014 |
| Obinutuzumab | Gazyva | CD20; Humanized IgG1; Glycoengineered | Chronic lymphocytic leukemia | 2014 | 2013 |
| Ofatumumab | Arzerra | CD20; Human IgG1 | Chronic lymphocytic leukemia | 2010 | 2009 |
| Panitumumab | Vectibix | EGFR; Human IgG2 | Colorectal cancer | 2007 | 2006 |
| Pembrolizumab | Keytruda | PD1; Humanized IgG4 | Melanoma | EC decision pending | 2014 |
| Pertuzumab | Perjeta | HER2; humanized IgG1 | Breast Cancer | 2013 | 2012 |
| Ramucirumab | Cyramza | VEGFR2; Human IgG1 | Gastric cancer | 2014 | 2014 |
| Rituximab | MabThera, Rituxan | CD20; Chimeric IgG1 | Non-Hodgkin lymphoma | 1998 | 1997 |
| Tositumomab-1131 | Bexxar | CD20; Murine IgG2a | Non-Hodgkin lymphoma | NA | 2003# |
| Trastuzumab | Herceptin | HER2; Humanized IgG1 | Breast cancer | 2000 | 1998 |

Source: Janice M. Reichert, PhD, Reichert Biotechnology Consulting LLC; table updated May 26, 2015 *,
Country-specific approval
Withdrawn or marketing discontinued for the first approved indication
NA, not approved or in review "Anticancer therapy" as used herein refers to conventional cancer treatments, including chemotherapy and radiotherapy, as well as immunotherapy and vaccine therapy.

The term "anti-chemorepellant effect" refers to the effect of the anti-chemorepellant agent to attenuate or eliminate the chemorepellant effect of the chemokine.

"Cancer" refers to a disease caused by an uncontrolled division of abnormal cells in a part or parts of the body. The term "tumor" refers to an abnormal mass of tissue. A tumor can be benign or malignant (cancerous). A tumor may be solid or liquid. Examples of solid tumors include: adrenal cancer, anal cancer, bile duct cancer, bladder cancer, bone cancer, brain/CNS tumors, breast cancer, e.g., inflammatory breast cancer, cancer of unknown primary (CUP), Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, head and neck cancer, Hodgkin disease, Kaposi sarcoma, kidney cancer, laryngeal and hypopharyngeal cancer, liver cancer, lung cancer (e.g., non-small cell lung cancer, small cell lung cancer, lung carcinoid tumor), lymphoma of the skin, malignant mesothelioma, nasal lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma, skin cancer (e.g., basal and squamous cell, melanoma), Merkel cell carcinoma, small intestine cancer, stomach cancer, testicular cancer, thymus cancer, thyroid cancer, uterine sarcoma, vaginal cancer, vulvar cancer, Waldenstrom macroglobulinemia, and Wilms' tumor. Examples of non-solid tumors include: leukemia (e.g., acute lymphocytic leukemia (ALL), acute myeloid leukemia (AML), chronic lymphocytic leukemia (CLL), chronic myeloid leukemia (CML), chronic myelomonocytic lymphoma (CMML), multiple myeloma, and myelodysplastic syndrome. In some embodiments, the cancer is breast cancer, more preferable inflammatory breast cancer.

"CD3" as used herein, also known as 'cluster of differentiation 3' is a protein complex and is composed of four distinct chains. In mammals, the complex contains a CD3γ chain, a CD3δ chain, and two CD3ε chains. These chains associate with the T-cell receptor (TCR) and the ζ-chain to generate an activation signal in T lymphocytes. The TCR, ζ-chain, and CD3 molecules together comprise the TCR complex.

By "chemorepellant activity" or "chemorepellant effect" it is meant the ability of an agent to repel (or chemorepel) a eukaryotic cell with migratory capacity (i.e., a cell that can move away from a repellant stimulus), as well as the chemorepellant effect of a chemokine secreted by a cell, e.g., a tumor cell. Usually, the chemorepellant effect is present in an area around the cell wherein the concentration of the chemokine is sufficient to provide the chemorepellant effect. Some chemokines, including interleukin 8 and CXCL12, may exert chemorepellant activity at high concentrations (e.g., over about 100 nM), whereas lower concentrations exhibit no chemorepellant effect and may even be chemoattractant.

Accordingly, an agent with chemorepellant activity is a "chemorepellant agent." Such activity can be detected using any of a variety of systems well known in the art (see, e.g., U.S. Pat. No. 5,514,555 and U.S. Patent Application Pub. No. 2008/0300165, each of which is incorporated by reference herein in its entirety). A preferred system for use herein is described in U.S. Pat. No. 6,448,054, which is incorporated herein by reference in its entirety.

"Chemotherapeutic agent" or "chemotherapeutic compound" is a chemical compound useful in the treatment of cancer.

"Chimeric antigen receptors" or "CARs" refer to fusion proteins comprised of an antigen recognition moiety and T-cell activation domains. Eshhar et al., (1993) Proc. Natl. Acad. Sci., 90(2): 720-724. A CAR is an artificially constructed hybrid protein or polypeptide containing an antigen binding domain of an antibody (e.g., a single chain variable fragment (scFv)) linked to T-cell signaling or T-cell activation domains CARs have the ability to redirect T-cell specificity and reactivity toward a selected target (i.e., a tumor cell) in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains.

The term "comprising" or "comprises" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

The phrase "concurrently administering" refers to administration of at least two agents to a patient over a period of time. As used herein, the word "concurrently" means sufficiently close in time to produce a combined effect (that is, concurrently can be simultaneously, or it can be two or more events occurring within a short time period before or after each other). Concurrent administration includes, without limitation, separate, sequential, and simultaneous administration.

"Control" or "reference" as used herein is a standard of comparison. For example, the level of CXCL12 or FoxP3 in a neoplasia may be compared to the level of CXCL12 or FoxP3, respectively, in a corresponding normal or healthy tissue or, e.g., the level of CXCR4 in modified NK-92 cell may be compared to the level of CXCR4 in an unmodified NK-92 cell.

"CXCR4," as used herein, refers to the CXCR4 chemokine receptor, a receptor in the GPCR (G-protein coupled receptor) gene family, which is expressed by cells in the bone marrow, immune system and the central nervous system. In response to binding its ligand CXCL12 or SDF-1α (stromal cell-derived factor-1α), CXCR4 is thought to trigger the migration and recruitment of immune cells, as well as the homing of stem cells (e.g., EPCs). The receptor is believed to enhance downstream signaling by several different pathways. As a GPCR, CXCR4 binding of CXCL12 activates G-protein mediated signaling, including downstream pathways such as ras, and PI3 kinase. PI3 kinase activated by CXCL12 and CXCR4 plays a role in lymphocyte chemotaxis in response to these signals. One endpoint of CXCR4 signaling is the activation of transcription factors such as AP-1 and chemokine regulated genes. JAK/STAT signaling pathways also appear to play a role in CXCL12/CXCR4 signaling. The sequence and structure of the human CXCR4 is known; see e.g., GenBank Accession Nos. NM 003467 and NM 001008540 for the nucleotide sequence and NP 003458. The nucleotide and polypeptide sequences of human SDF-1α are set forth in GenBank Accession Nos. NM 000609 and NP 000600, respectively. See, Hwang, J. H. et al. (2003) J. Clin. Endocrinol Metab. 88(1): 408-416; Babcock, G. J. et al. (2003) J. Biol. Chem. 278(5): 3378-3385; Barbouche, R. et al. (2003) J. Biol. Chem. 278 (5):3131-3136; Adams, G. B. et al. (2003) Blood 101(1):4551; Lapham, C. K. et al. (2002) J. Leukoc. Biol. 72(6): 12061214; Zhou, Y. et al. (2002) J. Biol. Chem. 277(51):4948149487; Sun, Y. et al. (2002) J. Biol. Chem. 277(51):4921249219; Bachelder, R. E. et al. (2002) Cancer Res. 62(24): 72037206; Barbero, S. et al. (2002) Ann. NY. Acad. Sci. 973:60-69; Rey, M. et al. (2002) J. Immunol. 169(10):54105414; Basmaciogullari, S. et al. (2002) J. Virol. 76(21): 10791-10800; Konig, R. R. et al. (2002) J. Virol. 76(21): 10627-10636; Martinez-Caceres, E. M. et al. (2002) Mult. Scler. 8(5):390-395; Odemis, V. et al. (2002) J. Biol. Chem. 277(42):3980139808; Moriuchi, M. et al. (2002) J. Infect. Dis. 186(8): 1194-1197; Kollet, O. et al. (2002) Blood 100(8): 2778-2786; Libura, J. et al. (2002) Blood 100(7):2597-2606; Honczarenko, M. et al. (2002) Blood 100(7):2321-2329; Ptasznik, A. et al. (2002) J. Exp. Med. 196(5): 667678; Estes, J. D. et al. (2002) J. Immunol. 169(5):2313-2322; Farzan, M. et al. (2002) J. Biol. Chem. 277 (33):29484-29489; Fotopoulos, G. et al. (2002) Proc. Natl. Acad. Sci. U.S.A. 99(14):94109414; Peled, A. et al. (2002) Stem Cells 20(3):259-266; Habasque, C. (2002) Mol. Hum. Reprod. 8(5):419-425; Zhou, N. et al. (2002) J. Biol. Chem. 277(20):1747617485; Lu, M. et al. (2002) Proc. Natl. Acad. Sci. U.S.A. 99(10):7090-7095; Valenzuela-Fernandez, A. et al. (2002) J. Biol. Chem. 277 (18): 15677-15689; Schrader, A. J. et al. (2002) Br. J. Cancer 86(8):1250-1256; Nguyen, D. H. and Taub, D. (2002) J. Immunol. 168(8): 4121-4126; Salvucci, O. et al. (2002) Blood 99(8):2703-2711; Juffermans, N. P. et al. (2002) J. Infect. Dis. 185(7): 986-989; Taichman, R. S. et al. (2002) Cancer Res. 62(6): 18321837; Zamarchi, R. et al. (2002) Clin. Exp. Immunol. 127(2):321-330; Arthos, J. et al. (2002) Virology 292(1): 98-106; Ferraro, G. A. et al. (2001) AIDS Res. Hum. Retroviruses 17(13):1241-1247; Ullrich, C. K. et al. (2000) Blood 96(4):1438-1442; Poznansky, M. C. et al. (2000) Nat. Med. 6(5):543-548; Secchiero, P. et al. (2000) J. Immunol. 164(8): 4018-4024; Cheng, Z. J. et al. (2000) J. Biol. Chem. 275(4): 2479-2485; Lalani, A. S. et al. (1999) Science 286(5446): 1968-1971; Sotsios, Y. et al. (1999) J. Immunol. 163(11): 5954-5963; Gupta, S. K. and Pillariseffi, K. (1999) J. Immunol. 163(5):2368-2372; Klein, R. S. et al. (1999) J.

Immunol. 163(3): 1636-1646; Ling, K. et al. (1999) Proc. Natl. Acad. Sci. U.S.A. 96(14):7922-7927; Yasukawa, M. et al. (1999) J. Immunol. 162(9):5417-5422; Zou, Y. R. et al. (1998) Nature 393(6685):595-599; Tachibana, K. et al. (1998) Nature 393(6685):591-594; Caruz, A. et al. (1998) FEBS Lett. 426(2):271-278; Moriuchi, M. et al. (1997) J. Immunol. 159(9):4322-4329; Bleul, C. C. et al. (1996) Nature 382(6594):829-833; Choe, H. et al. (1996) Cell 85(7):11351148; Lu, Z. H. et al. (1995) J. Biol. Chem. 270(44):2623926245; Loetscher, M. et al. (1994) J. Biol. Chem. 269(1):232237; Nomura, H. et al. (1993) Int. Immunol. 5(10): 12391249; Jazin, E. E. et al. (1993) Regul. Pept. 47(3):247-258; Herzog, H. et al. (1993) DNA Cell Biol. 12(6):465-471; Federsppiel, B. et al. (2993) Genomics 16(3):707-712 (1993); Bleul, C. C. et al. (1996) Nature 382(6594):829-33); Cheng, Z. et al. (2000) J. Biol. Chem. 275(4):2476-2485; Dutt, P. et al. (1998) J. Immunology. 161: 36523658; Wang, J. F. et al. (2000) Blood 95(8):2505-13; Ling K. et al. (1999) Cell Biology 96:7922-7927; Vicente-Manzanares, M. et al. (1999) Immunology 163:4001-12; Ganju, R. K. et al. (1998) Biological Chemistry 273(36): 23169-175; and Zhang, X. F. et al. (2001) Blood 97(11): 3342-3348; Glodek, A. M. et al. (2003) J. Exp. Med. 197(4):461-473; Roland, J. et al. (2003) Blood 101(2):399-406; Adamns, G. B. (2003) Blood 101(1):45-51; Sun, Y. et al. (2002) J. Biol. Chem. 277(50:49212-49219; Krug, A. et al. (2002) J. Immunol. 169(11):6079-6083; Barbero, S. et al. (2002) Ann. N.Y. Acad. Sci. 973:60-69; Nance, C. L. and Shearer, W. T. (2002) Clin. Immunol. 105(2):208-214; Libura, J. et al. (2002) Blood 100 (7):2597-2606; Honczarenko, M. (2002) Blood 100(7):23212329; Netelenbos, T. (2002) J. Leukoc. Biol. 72(2):353-362; Farzan, M. et al. (2002) J. Biol. Chem. 277(33):29484-29489; Okabe, S. et al. (2002) E. Hematol. 30(7):761-766; Langford, D. (2002) J Neuroimmunol. 127(1-2):115-126; Inngjerdingen, M. et al. (2002) Blood 99(12):4318-4325; Lee, Y. (2002) 99(12): 4307-4317; Peled, A. (2002) Stem Cells 20(3):259-266; Wright, N. et al. (2002) J. Immunol. 168(10): 5268-5277; Valenzuela-Fernandez, A. (2002) J. Biol. Chem. 277(18): 15677-15689; Schrader, A. J. et al. (2002) Br. J. Cancer 86(8): 1250-1256; Salvucci, O. et al. (2002) Blood 99(8): 2703-2711; Taichman, R. S. et al. (2002) Cancer Res. 62(6):1832-1837; Zaitseva, M. et al. (2002) J. Immunol. 168 (6):2609-2617; Casamayor-Palleja, M. et al. (2002) Blood 99(6): 1913-1921; Phillips, R. and Ager, A. (2002) Eur. J. Immunol. 32(3):837-847; Tresoldi, E. et al. (2002) J. Infect. Dis. 185(5):696-700; Riabov, G. S. et al. (2002) Genetika 38(2):278-280; Lataillade, J. J. et al. (2002) Blood 99(4): 11171129; Nanki, T. and Lipsky, P. E. (2001) Cell. Immunol. 214(2):145-154; Lathey, J. L. et al. (2001) J. Infect. Dis. 184(11):1402-1411; Bajetto, A. et al. (2001) J. Neurochem. 77(5): 1226-1236; Poznansky, M. C. et al. (2000) Nat. Med. 6(5):543-548; Ghezzi, S. et al. (2000) Biochem. Biophys. Res. Commun. 270(3):992-996; Cheng, Z. J. et al. (2000) J. Biol. Chem. 275(4):2479-2485; Luttichau, H. R. et al. (2000) J. Exp. Med. 191(1):171-180; Lalani, A. S. et al. (1999) Science 286(5446):1968-1971; Sotsios, Y. et al. (1999) J. Immunol. 163(11):5954-5963; Vicente-Manzanares, M. et al. (1999) J. Immunol. 163(7):4001-4012; Kozak, S. L. et al. (1999) J. Biol. Chem. 274(33):23499-23507; Su, S. B. et al. (1999) J. Immunol. 162(12):7128-7132; Weber, K. S. et al. (1999) Mol. Biol. Cell 10(4):861-873; Zaitseva, M. B. et al. (1998) J. Immunol. 161(6):3103-3113; Rubbert, A. et al. (1998) J. Immunol. 160(8):3933-3941; Bleul, C. C. et al. (1996) Nature 382(6594):829-833; and Shirozu, M. et al. (1995) Genomics 28(3):495-500; and references cited therein.

"CXCR4/CXCL12 antagonist" or "CXCR7/CXCL12 antagonist" refers to a compound that antagonizes CXCL12 binding to CXCR4 and/or CXCR7 or otherwise reduces the chemorepellant effect of CXCL12.

"Cytokine" is a generic term for non-antibody, soluble proteins which are released from one cell subpopulation and which act as intercellular mediators, for example, in the generation or regulation of an immune response. See Human Cytokines: Handbook for Basic & Clinical Research (Aggrawal, et al. eds., Blackwell Scientific, Boston, Mass. 1991) (which is hereby incorporated by reference in its entirety for all purposes).

"Decrease," "reduced," and "reduction" are all used herein generally to mean a decrease by a statistically significant amount. However, for avoidance of doubt, "decrease," "reduced," and "reduction" means a decrease by at least 10% as compared to a reference or control level, for example a decrease by at least about 20%, or at least about 30%, or at least about 40%, or at least about 50%, or at least about 60%, or at least about 70%, or at least about 80%, or at least about 90% or up to and including a 100% decrease (i.e., absent level as compared to a reference or control sample), or any decrease between 10-100% as compared to a reference or control level.

"Efficacy" as used herein refers to the effectiveness of a particular treatment regime. Efficacy can be measured based on such characteristics (but not limited to these) as inhibition of solid or liquid tumor growth, reduction of tumor mass, reduction of metastatic lesions as assessed, for example, by radiologic imaging, slowed tumor growth, and lack of detectable tumor associated antigens. Additional methods of assessing tumor progression are discussed herein and would be known to the treating and diagnosing medical professionals.

The term "immortalized" or "immortalized cells" as used herein refers to NK cells that have been immortalized in vitro. That is, they are capable of growth and proliferation in in vitro cell culture. Examples include NK-92 cells.

"Immune cells" as used herein are cells of hematopoietic origin that are involved in the specific recognition of antigens Immune cells include antigen presenting cells (APCs), such as dendritic cells or macrophages, B cells, T cells, and the like. Immune cells further include natural killer (NK) cells.

"Increased," "increase," "enhance," or "activate" are all used herein to generally mean an increase by a statically significant amount. For the avoidance of any doubt, the terms "increased," "increase," "enhance," or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "kill" with respect to a cell/cell population is directed to include any type of manipulation that will lead to the death of that cell/cell population.

"Knock out" as used herein includes deleting all or a portion of the target polynucleotide sequence, e.g., the CXCR4 sequence in a way that interferes with the function of the target polynucleotide sequence. For example, a knock out can be achieved by altering a CXCR4 polynucleotide sequence by inducing an insertion or a deletion in the CXCR4 polynucleotide sequence in a functional domain of the sequence (e.g., a CXCR4 binding domain). Those skilled in the art will readily appreciate how to use the CRISPR/Cas systems or other systems to knock out a CXCR4 polynucleotide sequence or a portion thereof.

"Metastatic disease," "metastases," and "metastatic lesion" as used herein are meant a group of cells which have migrated to a site distant relative to the primary tumor.

"NK cell" (natural killer cells) as used herein are a type of cytotoxic lymphocyte critical to the innate immune system.

"NK-29 cell" as used herein is a commercially available human cell line with the phenotypical and functional characteristics of activated natural killer cells. It is a continuously growing cell line that can be expanded to large numbers and is effective in killing tumor cells (see Gong et al., Leukemia 8(4): 652-658 (April 1994)). NK-92 cell are available from, e.g., American Type Culture Collection. NK-92 cells may be genetically modified ex vivo to express another molecule, e.g., Fc receptor such as CD16, on its surface, see e.g., U.S. Pat. No. 8,313,943, or modified to express interleukin-2 (IL-2), see e.g., U.S. Pat. No. 8,034,332.

"Optional" or "optionally" means that the subsequently described event or circumstance can or cannot occur, and that the description includes instances where the event or circumstance occurs and instances where it does not.

"Patient," "subject," "individual," and the like as used herein are used interchangeably herein, and refer to any animal, or cells thereof whether in vitro or in situ, amenable to the methods described herein. In one embodiment, the patient, subject, or individual is a mammal. In some embodiments, the mammal is a mouse, a rat, a guinea pig, a non-human primate, a dog, a cat, or a domesticated animal (e.g., horse, cow, pig, goat, sheep). In some embodiments, the patient, subject or individual is a human.

"Pharmaceutically acceptable composition" refers to a composition that is suitable for administration to a mammal, particularly, a human.

The term "prevent" or "preventative" as used herein means a prophylactic treatment. A preventative effect is obtained by delaying the onset of a disease state or decreasing the severity of a disease state when it occurs.

The term "separate" administration refers to an administration of at least two active ingredients at the same time or substantially the same time by different routes and/or in different compositions.

"Sequential" administration refers to administration of at least two active ingredients at different times, the administration route being identical or different. More particularly, sequential use refers to the whole administration of one of the active ingredients before administration of the other or other commences. It is thus possible to administer one of the active ingredients over several minutes, hours, or days before administering the other active ingredient or ingredients. There is no simultaneous treatment in this case.

"Simultaneous" therapeutic use refers to the administration of at least two active ingredients by the same route and at the same time or at substantially the same time.

"Systemic administration," "administered systemically," "peripheral administration," and "administered peripherally" as used herein refer to the administration of a population of cells other than directly into a target site, tissue, or organ, such that it enters, instead, the patient's circulatory system and, thus, is subject to metabolism and other like processes.

It is also to be appreciated that the various modes of treatment or prevention of medical diseases and conditions as described are intended to mean "substantial," which includes total but also less than total treatment or prevention, and wherein some biologically or medically relevant result is achieved.

"T cells" or "T lymphocytes," as used herein, are a type of lymphocyte, i.e., a type of white blood cell, that plays a central role in cell-mediated immunity, and can be distinguished from other lymphocytes, such as B cells and natural killer cells (NK cells), by the presence of a T-cell receptor (TCR) on the cell surface. T cells or T lymphocytes include several subsets of T cells, each having a distinct function. The majority of human T cells rearrange their alpha/beta T cell receptors and are termed alpha beta T cells and are part of adaptive immune system. Specialized gamma delta T cells, which comprise a minority of T cells in the human body (more frequent in ruminants), have invariant TCR (with limited diversity), can effectively present antigens to other T cells and are considered to be part of the innate immune system.

"T cell receptor" or "TCR" is a complex of integral membrane proteins that participate in the activation of T-cells in response to an antigen. Stimulation of TCR is triggered by MHC (major histocompatibility complex) molecules on cells with the antigen. Engagement of the TCR initiates positive and negative cascades that ultimately result in cellular proliferation, differentiation, cytokine production, and/or activation-induced cell death. These signaling cascades regulate T-cell development, homeostasis, activation, acquisition of effector's functions and apoptosis.

The term "therapeutic" as used herein means a treatment. A therapeutic effect is obtained by suppression, remission, or eradication of a disease state.

The term "therapeutically effective amount," "prophylactically effective amount," or "effective amount" refers to an amount of the agent that, when administered, is sufficient to cause the desired effect. For example, an effective amount of modified NK cells of this invention is an amount that inhibits or reduces the growth or progression or metastasis of a tumor. The therapeutically effective amount of the agent will vary depending on the tumor being treated and its severity as well as the age, weight, etc., of the patient to be treated. One of skill in the art will be able to determine appropriate dosages depending on these and other factors. The modified NK cells of this invention may be administered with or without another conventional anticancer treatment and/or anti-chemorepellant treatment and can also be administered in combination with one or more additional therapeutic compounds to inhibit or reduce the growth progression and/or metastasis of a tumor.

"Treating," and "treatment," and the like are used herein to generally mean obtaining a desired pharmacological and physiological effect. More specifically, the reagents described herein which are used to treat a subject with a solid or liquid tumor and/or metastatic disease generally are provided in a therapeutically effective amount to achieve any one or more of the following: inhibited tumor growth, reduction in tumor mass, loss of metastatic lesions, inhibited development of new metastatic lesions after treatment has started, or reduction in tumor such that there is no detectable disease (as assessed by e.g., radiologic imaging, biological fluid analysis, cytogenetics, fluorescence in situ hybridization, immunocytochemistry, colony assays, multi-parameter flow cytometry, or polymerase chain reaction). The term "treatment," as used herein, covers any treatment of a disease in a mammal, particularly a human.

"Tumor" as used herein is meant to include both benign and malignant growths or cancer. Thus, the term "cancer", unless otherwise stated, can include both benign and malignant growths. By "liquid tumor" is meant a liquid and/or soft tissue tumor, such as a leukemia or a bone cancer.

Modified NK Cells

Natural killer (NK) cells are a type of cytotoxic lymphocyte critical to the innate immune system. NK cells are triggered to exert a cytotoxic effect directly against a target cell upon binding or ligation of an activating NK cell receptor to the corresponding ligand on the target cell. The cytotoxic effect is mediated by secretion of a variety of cytokines by the NK cells, which in turn stimulate and recruit other immune system agents to act against the target. Activated NK cells also lyse target cells via the secretion of the enzymes perforin and granzyme, stimulation of apoptosis-initiating receptors, and other mechanisms.

NK cells have been evaluated as an immunotherapeutic agent in the treatment of certain cancers. NK cells used for this purpose may be autologous or non-autologous (i.e., from a donor).

In one embodiment, the NK cells used in the compositions and methods herein are autologous NK cells. In one embodiment, the NK cells used in the compositions and methods herein are non-autologous NK cells.

NK-92 cells are a continuously growing NK cell line that can be expanded to large numbers and is effective in killing tumor cells (see Gong et al., Leukemia Vol. 8(4) PP 652-658 (April 1994) and Klingemann H-G. Development and testing of NK cell lines. In Lotze M T & Thompson A W (eds): Natural killer cells—Basic Science and Clinical applications (2010): 169-75). NK-92 cells are commercially available from, e.g., American Type Culture Collection. Other NK cell lines include NK-YS, KHYG-1, NKL, NKG, SNK-6, and IMC-1. See, Klingemann et al. Front Immunol. 2016; 7: 91, which is incorporated herein by reference in its entirety. Without wishing to be bound by theory, it is contemplated that the immune system of a patient having a tumor has lost its ability to recognize tumor and/or to effectively attack and eliminate the tumor. Supplementing such a patient's immune system by the administration of immune cells that have the ability to inhibit the growth, progression and/or metastasis of a tumor should improve the patient's immune response to the tumor and enhance the patient's overall survival. In fact, the effectiveness of NK-92 cells for treating tumors, e.g., refractory or relapsed acute myeloid leukemia and Merkel cell carcinoma, and hematological malignancies is being investigated in clinical trials.

Examples of NK-92 cells are available from the American Type Culture Collection (ATCC) as ATCC CRL-2407. Examples of genetically modified NK-92 cells are available from ATCC as ATCC CRL-2408, ATCC CRL-2409, PTA-6670, PTA-6967, PTA8837, and PTA-8836.

An aspect of the invention described herein is an ex vivo modified NK cell having no or substantially reduced levels of CXCR4 expression on the surface of the cells. The term "substantially reduced levels" refers to a level of functional CXCR4 expression that is less than 50% of the average functional CXCR4 expression level in NK cells, e.g., less than about 40%, 30%, 20%, 10%, 5%, or 1%. Such modified NK cells may be generated by reducing the expression levels of the CXCR4 gene, or by modifying the CXCR4 protein such that the modified protein exhibits reduced stability, binding activity to CXCL12, intracellular trafficking and recycling, and/or membrane localization. Expression may be reduced by modifying the nucleotide sequence of the CXCR4 regulatory, coding or non-coding sequences, or by altering expression of CXCR4, e.g., via short interfering RNAs (siRNAs), short hairpin RNAs (shRNAs) or microRNAs (miRNAs). The CXCR4 gene may be modified using any suitable method known in the art, including but not limited to, e.g., gene silencing and/or gene editing techniques including, e.g., small interfering RNAs, ZFN, TALEN, and CRISPR. RNAi (e.g., siRNA) is a ubiquitous, highly specific, endogenous and evolutionarily conserved mechanism used to modify gene expression and is increasingly being used for therapeutic applications. siRNAs are 21-23 nucleotide (nt), double stranded molecules (dsRNA), with symmetric 2-3 nt 3' overhangs and 5'-phosphate and 3'-hydroxyl groups, that mediate the cleavage and subsequent degradation of complementary mRNA sequences and thus regulate gene expression. RNAi technology, such as siRNA, has already been shown to modulate specific gene expression in cancer cells with subsequent tumor regression. (Joao Conde, et al., Materials Today (August 2015); doi: 10.1016/j.mattod.2015.07.005). ZNF, TALEN and CRISPR use endonucleases that initiate double-strand breaks (DSBs) at virtually any genomic target sequence, and are used for many applications, including gene knockout, transgene knock-in, gene tagging, and correction of genetic defects. See e.g., Gaj et al., (July 2013) Trends Biotechnol. 31(7): 397-405; Jinek et al., (August 2012) Science 337(6096): 816-21, Jinek et al., eLife 2:e00471 (2013), and Calsten and Childs, (June 2015) Frontiers in Immunology, 6(Article 266):1-9; Moscou and Bogdanove (2009) Science 326:1501; Boch J, et al. (2009) Science 326:1509-1512; Römer P, et al. (2010) New Phytol. 187:1048-1057 and; Christian M, et al. (2010) Genetics 186:757-761; 89; Perez E E, et al. (2008); 26(7):808-816; Tebas P, et al. (2014) N Engl J Med.; 370(10):901-910; Holt N, et al. (2010) Nat Biotechnol. 28(8):839-847. 92. Genovese P, et al. (2014) Nature, 510 (7504):235-240. 93. Schwank G, et al. (2013) Cell Stem Cell 13(6):653-658.

In an aspect of this invention, the NK cell that is modified and used in the methods and compositions described herein is an NK-92 cell, an NK-YS cell, a KHYG-1 cell, an NKL cell, an NKG cell, an SNK-6 cell, or an IMC-1 cell.

Also an aspect of the invention described herein is an ex vivo modified NK cell expressing or overexpressing CXCR7 on the surface of the cells. The term "overexpressing" as used herein refers to a level of expression that is greater than the average level of expression of CXCR7 on NK cells, e.g., at least about 10%, 20%, 30%, 40%, or 50% greater or more. CXCR7 may be introduced into the NK cells by any method known in the art, e.g., ZNF, TALEN and CRISPR techniques.

The modified NK cells of this invention include modified NK cells, e.g., NK-92 cells, that are modified to express CD-16 or IL-2 (see U.S. Pat. Nos. 8,034,332 and 8,313,943). The NK cells may be modified using any method known in the art, e.g., by silencing the CXCR4 gene via interfering RNA technology, or by gene editing. As used herein, the term "gene editing" refers to a reverse genetics method using artificially engineered nucleases to cut and create specific double-stranded breaks at a desired location(s) in the genome, which are then repaired by cellular endogenous processes such as, homologous recombination (HR), homology directed repair (HDR) and non-homologous end-joining (NHEJ). NHEJ directly joins the DNA ends in a double-stranded break, while HDR utilizes a homologous sequence as a template for regenerating the missing DNA sequence at the break point.

It is contemplated herein that the Cas9/CRISPR system of genome editing be employed with the methods and compositions described herein. Clustered regularly interspaced short palindromic repeats (CRISPR)/CRISPR-associated (Cas) systems is useful for RNA-programmable genome editing (see e.g., Cong, L., et al., (2013) Science. 339, 81923; Ding, Q., et al., Cell Stem Cell. 12, 393-4. (2013); Gilbert, L. A. et al. (2013) Cell, 154, 442-451; Jinek, M., et al., (2013), Elife. 2, e00471; Li, D., et al., (2013) Nat Biotechnol. 31, 681-3; Liu H., et al., (July 2015) Bioinformatics 31(22):3676-3678; Mali, P., et al., (2013) Science. 339, 823-; Niu, Y., et al., Cell. 156, 836-43 (2014); Qi, L. S. et al. (2013) Cell, 152, 1173-1183; Ran, F. A., et al., (2013) Cell. 154, 1380-9; Wang, H., et al., (2013) Cell. 153, 910-8, U.S. publication 20150176013.

Alternatively, it is contemplated that gene editing is performed using recombinant adeno-associated virus (rAAV) based genome engineering, which is a genome-editing platform centered around the use of rAAV vectors that enables insertion, deletion or substitution of DNA sequences into the genomes of live mammalian cells. The rAAV genome is a single-stranded deoxyribonucleic acid (ssDNA) molecule, either positive- or negative-sensed, which is about 4.7 kilobases long. These single-stranded DNA viral vectors have high transduction rates and have a unique property of stimulating endogenous homologous recombination in the absence of causing double strand DNA breaks in the genome. One of skill in the art can design a rAAV vector to target a desired genomic locus and perform both gross and/or subtle endogenous gene alterations in a cell, such as a deletion. rAAV genome editing has the advantage in that it targets a single allele and does not result in any off-target genomic alterations. rAAV genome editing technology is commercially available, for example, the rAAV GENESIS™ system from Horizon™ (Cambridge, UK).

Also an aspect of this invention are pharmaceutical compositions comprising the modified NK cells described herein. In general, modified NK cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include, e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the NK cells as described herein using routine experimentation.

The modified NK cells and any other active ingredient can be mixed with excipients which are pharmaceutically acceptable and compatible with the active ingredient and in amounts suitable for use in the therapeutic methods described herein.

Additional agents included in a modified NK cell composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

Methods of Treatment

An aspect of this invention is a method for treating a subject in need thereof by administering the modified NK cells or pharmaceutical compositions comprising the modified NK cells of this invention, as the sole anticancer therapy, or in combination with one or more conventional anticancer therapies. Such conventional anticancer therapies include, e.g., chemotherapy, radiotherapy, hormonal therapy, and viral therapy as well as other immunotherapies and treatments with anti-chemorepellant agents.

The modified cell of this invention may be administered with one or more chemotherapeutic agent(s). Many chemotherapeutic agents useful in the treatment of various cancers are currently known in the art. Chemotherapeutic agents that are useful in the methods of this invention include, but are not limited to alkylating agents, antimetabolites, antitumor antibiotics, topoisomerase inhibitors, mitotic inhibitors, corticosteroids, and the like. Examples of chemotherapeutic drugs include but are not limited to: platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5fluorouracil (5-FU), azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel (taxol), docetaxel, etc.), topoisomerase inhibitors (e.g., irinotecan (CPT-11; Camptosar), topotecan, amsacrine, etoposide (VP 16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), tyrosine kinase inhibitors (e.g., gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), lefiunomide (SU101), vandetanib (Zactima™; ZD6474), etc.), pharmaceutically acceptable salts thereof, stereoisomers thereof, derivatives thereof, analogs thereof, and combinations thereof. Additional chemotherapy agents are listed, for example, in U.S. Patent Application Pub. No. 2008/0300165, which is incorporated herein by reference in its entirety.

Doses and administration protocols for chemotherapeutic agents are well-known in the art. One of skill in the art can readily determine the appropriate dosing regimen to be used, based on, e.g., the chemotherapeutic agent(s) administered, type of cancer being treated, stage of the cancer, age and condition of the patient, patient size, patient age, tumor size and location, and the like.

The modified NK cells may also be administered in combination with radiotherapy. Radiotherapy includes, e.g., external-beam radiation therapy, interstitial implantation of radioisotopes (I-125, palladium, iridium), radioisotopes such as strontium-89, thoracic radiation therapy, and intraperitoneal P-32 radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. Radiotherapy has been used in the treatment of a variety of cancers and the modified NK cells of this invention may be administered with one or more types of radiotherapeutic agents. Such agents include but are not limited to, X-rays, ultrasound, radiowaves, heat or magnetic fields, gamma rays, and charged particles. In one embodiment, the radiotherapeutic agent is delivered by a machine outside of the body (external-beam radiation therapy). The radiotherapeutic agent may be placed in close proximity to the tumor/cancer cells (brachytherapy) or the therapy may be a systemic radiation therapy.

External-beam radiation therapy may be administered by any means. Exemplary, non-limiting types of external-beam radiation therapy include linear accelerator-administered radiation therapy, 3-dimensional conformal radiation therapy (3D-CRT), intensity-modulated radiation therapy (IMRT), image-guided radiation therapy (IGRT), tomotherapy, stereotactic radiosurgery, photon therapy, stereotactic body radiation therapy, proton beam therapy, and electron beam therapy.

Internal radiation therapy (brachytherapy) may be by any technique or agent. In such therapy a radioactive source, e.g., radium-226 (Ra-226), cobalt-60 (Co-60), cesium-137 (Cs-137), cesium-131, iridium-192 (Ir-192), gold-198 (Au-198), iodine-125 (I-125), palladium-103, yttrium-90, etc., is placed inside the body close to cancer cells or a tumor mass. Such agents may be administered by seeds, needles, or any other route of administration, and may be temporary or permanent.

Systemic radiation therapy may be by any technique or agent. Exemplary, non-limiting types of systemic radiation therapy include radioactive iodine, ibritumomab tiuxetan (Zevalin®), tositumomab and iodine I 131 tositumomab (Bexxar®), samarium-153 lexidronam (Quadramet®), strontium-89 chloride (Metastron®), metaiodobenzylguanidine, lutetium-177, yttrium-90, strontium-89, and the like.

In one embodiment, a radiosensitizing agent is also administered to the patient. Radiosensitizing agents increase the damaging effect of radiation on cancer cells.

Doses and administration protocols for radiotherapy agents are well-known in the art. One of skill in the art can readily determine the proper dosing regimen to be used, based on factors including the agent(s) administered, type of cancer being treated, stage of the cancer, location of the tumor, condition of the patient, patient size and age, and the like.

In another aspect of the invention, the NK cells may be administered with an anti-chemorepellant agent. High concentrations of chemokines can have fugetactic (chemorepellant) effects on cells, whereas lower concentrations do not have such effects or even result in chemoattraction. For example, T-cells are repelled by CXCL12 via a concentration-dependent and CXCR4 receptor-mediated mechanism. The anti-chemorepellant agent may be any such agent known in the art, see e.g., the anti-chemorepellant agent as described in U.S. Patent Application Publication No. 2008/0300165, which is hereby incorporated by reference in its entirety.

Anti-chemorepellant agents include any agents that specifically inhibit chemokine and/or chemokine receptor dimerization, thereby blocking the chemorepellant response to a chemorepellant agent. Certain chemokines, including IL-8 and CXCL12, can also serve as chemorepellants at high concentrations (e.g., above 100 nM) where much of the chemokine exists as a dimer. Dimerization of the chemokine elicits a differential response in cells, causing dimerization of chemokine receptors, an activity which is interpreted as a chemorepellant signal. Blocking the chemorepellant effect of high concentrations of a chemokine secreted by a tumor can be accomplished, for example, by anti-chemorepellant agents which inhibit chemokine dimer formation or chemokine receptor dimer formation. For example, antibodies that target and block chemokine receptor dimerization, e.g., by interfering with the dimerization domains or ligand binding, can be anti-chemorepellant agents. Anti-chemorepellant agents that act via other mechanisms of action, e.g., that reduce the amount of chemorepellant cytokine secreted by the cells, inhibit dimerization, and/or inhibit binding of the chemokine to a target receptor, are also encompassed by the present invention. Where desired, this effect can be achieved without inhibiting the chemotactic action of monomeric chemokine.

In other embodiments, the anti-chemorepellant agent is a CXCR4 antagonist, CXCR7 antagonist, CXCR3 antagonist, CXCR4/CXCL12 antagonist, CXCR7/CXCL12 antagonist, or selective PKC inhibitor. Anti-chemorepellant agents may include, without limitation, molecules that inhibit expression of CXCL12 or CXCR4 or CXCR7 (e.g., antisense or siRNA molecules), molecules that bind to CXCL12 or CXCR4 or CXCR7 and inhibit their function (e.g., antibodies or aptamers), molecules that inhibit dimerization of CXCL12 or CXCR4 or CXCR7, and antagonists of CXCR4 or CXCR7.

The CXCR4 antagonist can be but is not limited to AMD3100 (plerixafor) or a derivative thereof, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, or TN14003, derivatives thereof, or an antibody that interferes with the dimerization of CXCR4. Additional CXCR4 antagonists are described, for example, in U.S. Patent Pub. No. 2014/0219952 and Debnath et al. Theranostics, 2013; 3(1): 47-75, each of which is incorporated herein by reference in its entirety, and include TG-0054 (burixafor), AMD3465, NIBR1816, AMD070, and derivatives thereof.

The CXCR3 antagonist can be but is not limited to TAK-779, AK602, or SCH-351125, or an antibody that interferes with the dimerization of CXCR3.

The CXCR4/CXCL12 antagonist can be but is not limited to tannic acid, NSC 651016, or an antibody that interferes with the dimerization of CXCR4 and/or CXCL12.

The CXCR7/CXCL12 antagonist can be but is not limited to CCX771, CCX754, or an antibody that interferes with the dimerization of CXCR7 and/or CXCL12.

The selective PKC inhibitor can be but is not limited to thalidomide or GF 109230X.

In one embodiment, the anti-fugetactic agent is AMD3100 (plerixafor). AMD3100 is described in U.S. Pat. No. 5,583,131, which is incorporated by reference herein in its entirety.

In one embodiment, the anti-chemorepellant agent is an AMD3100 derivative. AMD3100 derivatives include, but are not limited to, those found in U.S. Pat. Nos. 7,935,692 and 5,583,131 (USRE42152), each of which is incorporated herein by reference in its entirety.

In certain embodiments, the anti-chemorepellant agent is not an antibody. In certain embodiments, the anti-chemorepellant agent is not a heparinoid. In certain embodiments, the anti-chemorepellant agent is not a peptide.

In one embodiment, the anti-chemorepellant agent is coupled with a molecule that allows targeting of a tumor. In one embodiment, the anti-chemorepellant agent is coupled with (e.g., bound to) an antibody specific for the tumor to be targeted. In one embodiment, the anti-chemorepellant agent coupled to the molecule that allows targeting of the tumor is administered systemically.

In one embodiment, the anti-chemorepellant agent is administered in combination with an additional compound that enhances the anti-chemorepellant activity of the agent. In one embodiment, the additional compound is granulocyte colony stimulating factor (G-CSF). In one embodiment, G-CSF is not administered.

In an aspect of this invention, a population of NK cells comprising NK cells having an anti-chemorepellant agent bound to individual NK cells is administered to a patient having cancer, e.g., breast cancer, e.g., inflammatory breast cancer. In one embodiment, the anti-chemorepellant agent is bound to the cells through a receptor on the cell surface. In one embodiment, the receptor is CXCR4. In one embodiment, the receptor is CXCR7. In one embodiment, varying amounts of the anti-chemorepellant agent are bound to individual NK cells. In one embodiment, at least a portion of the receptors on each cell are occupied by the agent. In one embodiment, the anti-chemorepellant agent is bound to individual NK cells. In one embodiment, the NK cells are not modified to express no or substantially no CXCR4 on the cell surface. The term "modified NK cells" as used herein includes NK cells that have anti-chemorepellant agent bound thereto, regardless of whether the NK cells have been genetically modified.

In another aspect of this invention, the modified NK cell expressing no or substantially no CXCR4 is further modified to express a CAR. Such CAR-expressing modified NK cells may also be administered to a patient having a tumor in combination with a conventional anticancer therapy, e.g., hormonal therapy, radiotherapy, chemotherapy, immunotherapy, or viral therapy. For example, the modified cells may be administered in combination with a chemotherapeutic agent, or an anti-chemorepellant agent (e.g., AMD3100).

One aspect of the invention therefore includes ex vivo modified NK cells expressing no or substantially no CXCR4 or overexpressing CXCR7, or a combination of both, that are further modified to express a chimeric antigen receptor (CAR). In some embodiments, the modified NK cells are transformed with a nucleic acid encoding a CAR, wherein the CAR is expressed on the cell surface of the modified NK cells.

In one embodiment, the CAR is specific for a tumor-specific antigen. Tumor-specific antigens can also be referred to as cancer-specific or cancer-specific antigen. In one embodiment, the CAR is specific for a tumor-associated or cancer-associated antigen. A tumor-specific or cancer-specific antigen is a protein or other molecule that is unique to cancer cells, while a tumor-associated or cancer-associated antigen is an antigen that is highly correlated with certain tumor cells and typically are found at higher levels on a tumor cell as compared to on a normal cell. Tumor-specific antigens are described, by way of non-limiting example, in U.S. Pat. Nos. 8,399,645, 7,098,008; WO 1999/024566; WO 2000/020460; and WO 2011/163401, each of which is incorporated herein by reference in its entirety. In addition, examples of some known CARs are disclosure in Table 2. In one embodiment, the CAR targets a tumor-associated antigen selected from the group consisting of folate receptor-α, CAIX, CD19, CD20, CD30, CD33, CEA, EGP-2, erb-B2, erb-B 2,3,4, FBP, GD2, GD3, Her2/neu, IL-13R-a2, k-light chain, LeY, MAGE-A1, mesothelin, and PSMA.

In some embodiments, the CAR recognizes an antigen associated with a specific cancer type selected from the group consisting of ovarian cancer, renal cell carcinoma, B-cell malignancies, acute lymphoblastic leukemia (ALL), chronic lymphocytic leukemia (CLL), B-cell malignancies, refractory follicular lymphoma, mantle cell lymphoma, indolent B cell lymphoma, acute myeloid leukemia (AML), Hodgkin lymphoma, cervical carcinoma, breast cancer, e.g., inflammatory breast cancer, colorectal cancer, prostate cancer, neuroblastoma, melanoma, rhabdomyosarcoma, medulloblastoma, adenocarcinomas, and tumor neovasculature. In one embodiment, the CAR recognizes an antigen associated with breast cancer, and more preferably with inflammatory breast cancer.

TABLE 2

Chimeric Antigen Receptors

| Target antigen | Associated malignancy | Receptor type | CARs generation |
|---|---|---|---|
| Folate receptor-α | Ovarian cancer | ScFv-FcεRIγCAIX | First |
| CAIX | Renal cell carcinoma | ScFv-FcεRIγ | First |
| CAIX | Renal cell carcinoma | ScFv-FcεRIγ | Second |
| CD19 | B-cell malignancies | ScFv-CD3ζ (EBV) | First |
| CD19 | B-cell malignancies, CLL | ScFv-CD3ζ | First |
| CD19 | B-ALL | ScFv-CD28-CD3ζ | Second |
| CD19 | ALL | CD3ζ(EBV) | First |
| CD19 | ALL post-HSCT | ScFv-CD28-CD3ζ | Second |
| CD19 | Leukemia, lymphoma, CLL | ScFv-CD28-CD3ζ vs. CD3ζ | First and Second |
| CD19 | B-cell malignancies | ScFv-CD28-CD3ζ | Second |
| CD19 | B-cell malignancies post-HSCT | ScFv-CD28-CD3ζ | Second |
| CD19 | Refractory Follicular Lymphoma | ScFv-CD3ζ | First |

TABLE 2-continued

Chimeric Antigen Receptors

| Target antigen | Associated malignancy | Receptor type | CARs generation |
|---|---|---|---|
| CD19 | B-NHL | ScFv-CD3ζ | First |
| CD19 | B-lineage lymphoid malignancies post-UCBT | ScFv-CD28-CD3ζ | Second |
| CD19 | CLL, B-NHL | ScFv-CD28-CD3ζ | Second |
| CD19 | B-cell malignancies, CLL, BNHL | ScFv-CD28-CD3ζ | Second |
| CD19 | ALL, lymphoma | ScFv-41BB-CD3ζ Vs. CD3ζ | First and Second |
| CD19 | ALL | ScFv-41BB-CD3ζ | Second |
| CD19 | B-cell malignancies | ScFv-CD3ζ (Influenza MP-1) | First |
| CD19 | B-cell malignancies | ScFv-CD3ζ (VZV) | First |
| CD20 | Lymphomas | ScFv-CD28-CD3ζ | Second |
| CD20 | B-cell malignancies | ScFv-CD4-CD3ζ | Second |
| CD20 | B-cell lymphomas | ScFv-CD3ζ | First |
| CD20 | Mantle cell lymphoma | ScFv-CD3ζ | First |
| CD20 | Mantle cell lymphoma, indolent B-NHL | CD3ζ/CD137/CD28 | Third |
| CD20 | Indolent B cell lymphomas | ScFv-CD28-CD3ζ | Second |
| CD20 | Indolent B cell lymphomas | ScFv-CD28-41BBCD3ζ | Third |
| CD22 | B-cell malignancies | ScFV-CD4-CD3ζ | Second |
| CD30 | Lymphomas | ScFv-FcεRIγ | First |
| CD30 | Hodgkin lymphoma | ScFv-CD3γ (EBV) | First |
| CD33 | AML | ScFv-CD28-CD3ζ | Second |
| CD33 | AML | ScFv-41BB-CD3ζ | Second |
| CD44v7/8 | Cervical carcinoma | ScFv-CD8-CD3ζ | Second |
| CEA | Breast cancer | ScFv-CD28-CD3ζ | Second |
| CEA | Colorectal cancer | ScFv-CD3ζ | First |
| CEA | Colorectal cancer | ScFv-FcεRIγ | First |
| CEA | Colorectal cancer | ScFv-CD3ζ | First |
| CEA | Colorectal cancer | ScFv-CD28-CD3ζ | Second |
| CEA | Colorectal cancer | ScFv-CD28-CD3ζ | Second |
| EGP-2 | Multiple malignancies | scFv-CD3ζ | First |
| EGP-2 | Multiple malignancies | scFv-FcεRIγ | First |
| EGP-40 | Colorectal cancer | scFv-FcεRIγ | First |
| erb-B2 | Colorectal cancer | CD28/4-1BB-CD3ζ | Third |
| erb-B2 | Breast and others | ScFv-CD28-CD3ζ | Second |
| erb-B2 | Breast and others | ScFv-CD28-CD3ζ (Influenza) | Second |
| erb-B2 | Breast and others | ScFv-CD28mut-CD3ζ | Second |
| erb-B2 | Prostate cancer | ScFv-FcεRIγ | First |
| erb-B 2, 3, 4 | Breast and others | Heregulin-CD3ζ | Second |
| erb-B 2, 3, 4 | Breast and others | ScFv-CD3ζ | First |
| FBP | Ovarian cancer | ScFv-FcεRIγ | First |
| FBP | Ovarian cancer | ScFv-FcεRIγ (alloantigen) | First |
| Fetal acetylcholine receptor | Rhabdomyosarcoma | ScFv-CD3ζ | First |
| GD2 | Neuroblastoma | ScFv-CD28 | First |
| GD2 | Neuroblastoma | ScFv-CD3ζ | First |
| GD2 | Neuroblastoma | ScFv-CD3ζ | First |
| GD2 | Neuroblastoma | ScFv-CD28-OX40-CD3ζ | Third |
| GD2 | Neuroblastoma | ScFv-CD3ζ (VZV) | First |
| GD3 | Melanoma | ScFv-CD3ζ | First |
| GD3 | Melanoma | ScFv-CD3ζ | First |
| Her2/neu | Medulloblastoma | ScFv-CD3ζ | First |
| Her2/neu | Lung malignancy | ScFv-CD28-CD3ζ | Second |
| Her2/neu | Advanced osteosarcoma | ScFv-CD28-CD3ζ | Second |
| Her2/neu | Glioblastoma | ScFv-CD28-CD3ζ | Second |
| IL-13R-a2 | Glioma | IL-13-CD28-4-1BBCD3ζ | Third |
| IL-13R-a2 | Glioblastoma | IL-13-CD3ζ | Second |
| IL-13R-a2 | Medulloblastoma | IL-13-CD3ζ | Second |
| KDR | Tumor neovasculature | ScFv-FcεRIγ | First |
| k-light chain | B-cell malignancies | ScFv-CD3ζ | First |
| k-light chain | (B-NHL, CLL) | ScFv-CD28-CD3ζ vs. CD3ζ | Second |
| LeY | Carcinomas | ScFv-FcεRIγ | First |
| LeY | Epithelial derived tumors | ScFv-CD28-CD3ζ | Second |
| L1 cell adhesion molecule | Neuroblastoma | ScFv-CD3ζ | First |

TABLE 2-continued

Chimeric Antigen Receptors

| Target antigen | Associated malignancy | Receptor type | CARs generation |
|---|---|---|---|
| MAGE-A1 | Melanoma | ScFV-CD4-FcεRIγ | Second |
| MAGE-A1 | Melanoma | ScFV-CD28-FcεRIγ | Second |
| Mesothelin | Various tumors | ScFv-CD28-CD3ζ | Second |
| Mesothelin | Various tumors | ScFv-41BB-CD3ζ | Second |
| Mesothelin | Various tumors | ScFv-CD28-41BBCD3ζ | Third |
| Murine CMV infected cells | Murine CMV | Ly49H-CD3ζ | Second |
| MUC1 | Breast, Ovary | ScFV-CD28-OX40CD3ζ | Third |
| NKG2D ligands | Various tumors | NKG2D-CD3ζ | First |
| Oncofetal antigen (h5T4) | Various tumors | ScFv-CD3ζ (vaccination) | First |
| PSCA | Prostate carcinoma | ScFv-b2c-CD3ζ | Second |
| PSMA | Prostate/tumor vasculature | ScFv-CD3ζ | First |
| PSMA | Prostate/tumor vasculature | ScFv-CD28-CD3ζ | Second |
| PSMA | Prostate/tumor vasculature | ScFv-CD3ζ | First |
| TAA targeted by mAb IgE | Various tumors | FceRI-CD28-CD3ζ (+a-TAA IgE mAb) | Third |
| TAG-72 | Adenocarcinomas | scFv-CD3ζ | First |
| VEGF-R2 | Tumor neovasculature | scFv-CD3ζ | First |

The NK cells described herein can be genetically modified to express a CXCR7 and/or desired CAR by any method known in the art. A vector containing a polynucleotide encoding CXCR7 and/or a desired CAR can be readily introduced into the NK cells by physical, chemical, or biological means. Physical methods for introducing a polynucleotide into an immune cell, e.g., an NK cell, include calcium phosphate precipitation, lipofection, particle bombardment, microinjection, electroporation, and the like. Methods for producing modified cells comprising vectors and/or exogenous nucleic acids are well-known in the art. See, for example, Sambrook et al. (2001, Molecular Cloning: A Laboratory Manual, Cold Spring Harbor Laboratory, New York). Biological methods for introducing a polynucleotide of interest into an immune cell, e.g., an NK cell, include the use of DNA and RNA vectors. Viral vectors, and especially herpes viral vectors, lentiviral vectors and retroviral vectors, have become the most widely used method for inserting genes into mammalian, e.g., human cells. Other viral vectors can be derived from poxviruses, adenoviruses, and adeno-associated viruses, and the like. See, for example, U.S. Pat. Nos. 5,350,674 and 5,585,362. Chemical means for introducing a polynucleotide into an immune cell, e.g., an NK cell, include colloidal dispersion systems, such as macromolecule complexes, nanocapsules, microspheres, beads, and lipid-based systems including oil-in-water emulsions, micelles, mixed micelles, and liposomes. ZFN, TALEN and CRISPR may also be used for transgene knock-in. (See e.g., Gaj et al., (July 2013) Trends Biotechnol. 31(7):397-405; Jinek et al., (August 2012) Science 337 (6096):816-21, Jinek et al., eLife 2:e00471 (2013), and Calsten and Childs, (June 2015) Frontiers in Immunology, 6(Article 266):1-9; Moscou and Bogdanove (2009) Science 326:1501; Boch J, et al. (2009) Science 326:1509-1512; Römer P, et al. (2010) New Phytol 187:1048-1057 and; Christian M, et al. (2010) Genetics 186:757-761; 89; Perez E E, et al. (2008); 26(7):808-816; Tebas P, et al. (2014) N Engl J Med.; 370(10):901-910; Holt N, et al. (2010) Nat Biotechnol. 28(8):839-847. 92. Genovese P, et al. (2014) Nature, 510(7504):235-240. 93. Schwank G, et al. (2013) Cell Stem Cell. 13(6):653-658.)

In an embodiment of this invention, the NK cells modified to express a CXCR7 and/or a CAR are then contacted, mixed or otherwise combined with a predetermined amount of an anti-chemorepellant agent as described herein, e.g., AMD3100, under conditions such that the modified NK cells have overall anti-chemorepellant properties.

Tumors differ in the amount of chemorepellant chemokine that is produced by the tumor cells and/or present in the tumor microenvironment. The number of receptors for the chemorepellant chemokine expressed on the surface of an immune cell may also vary according to the individual, depending on factors including genetics, the amount of chemokine present (e.g., in the peripheral blood or in the microenvironment), type of immune cell, and other factors. Accordingly, and without being bound by theory, it is believed that the, amount of anti-chemorepellant agent that is required to counteract the chemorepellant effect of the tumor may depend on the amount of chemorepellant chemokine that is produced and/or the number of receptors expressed on immune cells.

Any method to determine the amount of anti-chemorepellant may be used. In one embodiment, a method for determining an effective local amount of an anti-chemorepellant agent for treating a tumor, based on the chemorepellant activity of the tumor and/or the receptor expression of at least a subset of immune cells, e.g., the modified NK cells of this invention, comprises: a) combining a plurality of mammalian tumor cells derived from a selected tumor, said plurality of cells having a defined tumor cell volume and a plurality of immune cells in a culture medium, and b) adding sequentially increasing known amounts of an anti-chemorepellant agent to said medium such that when an effective amount of the anti-chemorepellant agent is included in said medium, the immune cells will migrate toward said tumor cells. One of skill in the art can readily determine the amount of immune cells and chemorepellant agent to administer to a patient in need thereof based on the in vitro results.

The modified NK cell maybe contacted with the anti-chemorepellant agent to form a modified NK cells and anti-chemorepellant composition. Such composition can be stored under conditions known in the art for blood products for the subsequent administration to the patient. In one embodiment, the modified NK cells are stored under conditions known in the art for blood products, and then contacted with the anti-chemorepellant agent immediately prior to administration of the modified cells to the patient.

Dose and Administration

The modified NK cells described herein may be administered by any appropriate route which results in delivery to a desired location in the patient where at least a portion of the modified NK cells remain viable. The period of viability of the cells after administration to a subject can be as short as a few hours, e.g., twenty-four hours, to a few days, to as long as several years, i.e., long-term engraftment. For example, in some embodiments of the aspects described herein, an effective amount of modified NK cells is administered via a systemic route of administration, such as an intraperitoneal or intravenous route.

When provided prophylactically, the modified NK cells described herein can be administered to a subject in advance of any symptom of recurrence of the tumor. Accordingly, the prophylactic administration of the modified NK cells serves to reduce the recurrence of a tumor.

In an aspect of this invention, the modified NK cells and compositions comprising such modified cells, as described herein, are administered to the patient in effective amounts. The effective amount will depend upon the mode of administration, the particular stage of the tumor being treated and the desired outcome. It will also depend upon the physical condition, size and age of the subject, the nature of any concurrent therapy, and like factors well known to one of skill in the art. For therapeutic applications, an effective amount is the amount that is sufficient to achieve a medically desirable result, e.g., inhibition of growth, progression or metastasis of a tumor, or an increase in progression free survival and overall survival.

In one aspect of the invention, the modified NK cells are administered in combination with an anticancer agent or therapy, e.g., an anti-chemorepellant agent and/or other anticancer agent or therapy. In an aspect of this invention, the modified NK cells and anticancer agent are administered sequentially. That is, an amount of modified NK cells is administered for a period of time, and the anticancer agent is administered for a period of time following administration of the modified NK cells. In other embodiments, the anticancer agent is administered for a period of time sufficient to inhibit tumor growth, progression and/or metastasis, and the modified NK cells are administered for a period of time following administration of the anticancer agent. In some embodiments, the modified NK cells and the anti-chemorepellant agent are administered at the same time.

In an aspect of the invention, administration of the modified NK cells and anticancer agent is pulsatile. In one embodiment, an amount of modified NK cells is administered every 1 hour to every 24 hours, for example every 1 hour, 2 hours, 3 hours, 4 hours, 5 hours, 6 hours, 7 hours, 8 hours, 9 hours, 10 hours, 11 hours, 12 hours, 13 hours, 14 hours 15 hours, 16 hours, 17 hours, 18 hours, 19 hours, 20 hours, 21 hours, 22 hours, 23 hours, or 24 hours. In one embodiment, an amount of modified NK cell composition is administered every 1 day, 2 days, 3 days, 4 days, 5 days, 6 days, 7 days, 8 days, 9 days, or 10 days.

In an aspect of the invention, doses of the modified NK cells and an anticancer agent are administered in a pulsatile manner for a period of time to inhibit growth, progression, and/or metastasis of the tumor. In another aspect of the invention, the anticancer agent is an anti-chemorepellant agent and the agent is administered for a period of time sufficient to inhibit the chemorepellant effect of the tumor. In an embodiment, the period of time is between about 1 day and about 10 days. For example, the period of time may be 1 day, 2 days, 3 days, 4 days, 5 days, 6 days, 7 days, 8 days, 9 days, or 10 days.

In an aspect of the invention, an anticancer agent is administered after the period of time of administration of a modified NK cells and anticancer agent. In an embodiment, the anticancer agent is administered during a period of time wherein the chemorepellant effect of the cancer cells/tumor is attenuated by the modified NK cells composition. The length of time and modes of administration of the anticancer agent will vary, depending on the anticancer agent used, type of tumor being treated, age, size and condition of the patient, and the like. Determination of such parameters is within the capability of one of skill in the art.

In one embodiment, administration of the modified NK cell composition and anticancer agent is alternated. Preferably, the administration of the modified NK cells and anticancer agent is alternated until the condition of the patient improves. Improvement includes, without limitation, reduction in size of the tumor and/or metastases thereof, elimination of the tumor and/or metastases thereof, remission of the cancer, and/or reduction of at least one symptom of the cancer.

In one embodiment, the modified NK cells composition is administered parenterally. In one embodiment, the modified NK cell composition is administered, with or without an anticancer agent, via microcatheter into a blood vessel proximal to a tumor. In one embodiment, the modified NK cell composition, with or without an anticancer agent, is administered via microcatheter into a blood vessel within a tumor, or feeding directly into a tumor. In one embodiment, the modified NK cell composition, with or without an anticancer agent, is administered subcutaneously. In an embodiment of this invention, the modified NK cell composition, with or without an anticancer agent, is administered intradermally.

An additional aspect of this invention includes pump-based hardware delivery systems, some of which are adapted for implantation. Such implantable pumps include controlled-release microchips. A preferred controlled-release microchip is described in Santini, J T Jr. et al., Nature 1999, 397:335-338, the contents of which are expressly incorporated herein by reference.

It is contemplated that the treatment of tumors or cancers with an effective amount of modified NK cells with or without an anticancer agent for a period of time sufficient to inhibit the growth, progression and/or metastasis of a tumor will restore in whole or part the treated patient's immune defenses against tumors. Such treatment may also allow anticancer agents (e.g., chemotherapeutic agents, radiotherapeutic agents, other immunotherapeutic agents, hormonal agents, and the like) to better access the tumor or cancer in order to reduce or eradicate the tumor or cancer. Without being bound by theory, it is believed that co-administration of the modified NK cells of this invention in combination with anticancer agents as described herein will lead to a synergistic response in a patient with a tumor or cancer, such that the patient has a better outcome than with either therapy alone. Anticancer agents include, without limitation, traditional cancer therapies, e.g., chemotherapy, radiotherapy, immunotherapy, hormonal therapy, and/or vaccine therapy.

The modified NK cells of this invention may be administered with an anti-chemorepellant agent composition in combination with at least one other anticancer agent. "In combination" refers to any combination, including sequential or simultaneous administration. In one embodiment, the modified NK cells and anti-chemorepellant agent composition is administered separately from the anticancer agent. In one embodiment, the modified NK cells and anti-chemorepellant agent composition is administered in a single composition with the anticancer agent(s).

In one embodiment, the modified NK cells, with or without an anticancer agent, are administered intravenously, subcutaneously, orally, or intraperitoneally. In one embodiment, the modified NK cells, alone or in combination with one or more anticancer agent(s), are administered proximal to (e.g., near or within the same body cavity as) the tumor. In one embodiment, the modified NK cells, alone or in combination with one or more anticancer agent(s), are administered directly into the tumor or into a blood vessel feeding the tumor. In an embodiment, the modified NK cells, alone or in combination with one or more anticancer agent(s), are administered systemically. In another aspect of this invention, the modified NK cells, alone or in combination with one or more anticancer agent(s), are administered by microcatheter, or an implanted device, or an implanted dosage form.

In an aspect of this invention, the modified NK cells, alone or in combination with one or more anticancer agent(s), are administered in a continuous manner for a defined period. In another embodiment, the modified NK cells, alone or in combination with one or more anticancer agent(s), are administered in a pulsatile manner. For example, the modified NK cells, alone or in combination with one or more anticancer agent(s), may be administered intermittently over a period of time.

The modified NK cells and anti-anticancer agent(s) may be administered sequentially. For example, the modified NK cells may be administered for a period of time sufficient to inhibit growth, progression or metastasis of the tumor, and the anticancer agent can then be administered for a period of time to further inhibit the growth, progression or metastasis of the tumor.

In another aspect of this invention, the modified NK cells and anticancer agent(s) are administered sequentially in an alternating manner at least until the condition of the patient improves. Improvement of the condition of the patient includes, without limitation, inhibit the growth, progression or metastasis of the tumor, e.g., reduction in tumor size, a reduction in at least one symptom of the cancer, elimination of the tumor and/or metastases thereof, increased survival of the patient, and the like.

In an aspect of this invention, the modified NK cells and an anticancer agent(s) are administered directly to the tumor site. In another aspect of this invention, the modified NK cells and anticancer agent(s) are administered by direct injection into the tumor. In still another aspect of this invention, the modified NK cells and anticancer agent(s) are administered proximal to the tumor site. In one aspect, the modified NK cells and anticancer agent(s) are administered directly into a blood vessel associated with the tumor (e.g., via microcatheter injection into the blood vessels in, near, or feeding into the tumor). In some embodiments, the modified NK cells are administered in combination with an anti-chemorepellant agent.

NK Cell and NK-92 Cell Dosing

The amount of the modified NK cells and composition comprising the modified cells to be administered to the patient will depend, inter alia, on the type of NK cell that is used. Doses of autologous, allogenic, and/or immortalized NK cells are known in the art and can be determined by a qualified physician. In some embodiments, a reduced amount of cells may be used compared to a standard dose of NK cells that were not modified as described herein. Without being bound by theory, it is contemplated that improved targeting/penetration of the cells to the tumor will result in fewer total cells being required for treatment.

The modified NK cells of the present invention can be administered to a patient by absolute number of cells, for example, the patient can be administered from about $10^3$ cells to about $10^9$ cells, e.g., from about $10^3$ cells to about $10^4$ cells, from about $10^4$ cells to about $10^5$ cells, from about $10^5$ cells to about $10^6$ cells, from about $10^6$ cells to about $10^7$ cells, from about $10^7$ cells to about $10^8$ cells, or from about $10^8$ cells to about $10^9$ cells per injection, or any ranges between, end points inclusive.

In other embodiments, the amount of modified NK cells administered to a patient may be calculated by kg of body weight. In general, such amount is at least $1 \times 10^3$ modified NK cells per kg of body weight and most generally need not be more than $1 \times 10^9$ modified NK cells/kg, e.g., $1 \times 10^3$ cells/kg, $1 \times 10^4$ cells/kg, $1 \times 10^5$ cells/kg, $1 \times 10^6$ cells/kg, $1 \times 10^7$ cells/kg, $1 \times 10^8$ cells/kg, $1 \times 10^9$ cells/kg per injection, or any ranges between, end points inclusive.

The modified NK cells can be administered once to a patient who has or is suspected of having a cancer or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive. In some embodiments, the anti-chemorepellant agent is delivered for at least one day prior to administration of the modified immune cells.

Anti-chemorepellant Agent Dose and Administration

Generally, the dose of the modified NK cell composition of the present invention is from about 5 mg/kg body weight per day to about 50 mg/kg per day of the anti-chemorepellant agent, inclusive of all values and ranges there between, including endpoints. In one embodiment, the dose is from about 10 mg/kg to about 50 mg/kg per day. In one embodiment, the dose is from about 10 mg/kg to about 40 mg/kg per day. In one embodiment, the dose is from about 10 mg/kg to about 30 mg/kg per day. In one embodiment, the dose is from about 10 mg/kg to about 20 mg/kg per day. In one embodiment, the dose does not exceed about 50 mg/kg per day.

Where an anti-chemorepellant agent is administered in conjunction with the immune cells, the dose of the anti-chemorepellant agent may be from about 5 mg/kg body weight per day to about 50 mg/kg per day, inclusive of all values and ranges there between, including endpoints. In one embodiment, the dose is from about 10 mg/kg to about 50 mg/kg per day. In one embodiment, the dose is from about 10 mg/kg to about 40 mg/kg per day. In one embodiment, the dose is from about 10 mg/kg to about 30 mg/kg per day. In one embodiment, the dose is from about 10 mg/kg to about 20 mg/kg per day. In one embodiment, the dose does not exceed about 50 mg/kg per day.

In one embodiment, the dose of the modified NK cell composition and/or unbound anti-chemorepellant agent is from about 50 mg/kg per week to about 350 mg/kg per week of the anti-chemorepellant agent, inclusive of all values and ranges there between, including endpoints. In one embodiment, the dose is about 50 mg/kg per week. In one embodiment, the dose is about 60 mg/kg per week. In one embodiment, the dose is about 70 mg/kg per week. In one embodiment, the dose is about 80 mg/kg per week. In one embodiment, the dose is about 90 mg/kg per week. In one embodiment, the dose is about 100 mg/kg per week. In one embodiment, the dose is about 110 mg/kg per week. In one embodiment, the dose is about 120 mg/kg per week. In one embodiment, the dose is about 130 mg/kg per week. In one embodiment, the dose is about 140 mg/kg per week. In one embodiment, the dose is about 150 mg/kg per week. In one embodiment, the dose is about 160 mg/kg per week. In one embodiment, the dose is about 170 mg/kg per week. In one embodiment, the dose is about 180 mg/kg per week. In one embodiment, the dose is about 190 mg/kg per week. In one embodiment, the dose is about 200 mg/kg per week. In one embodiment, the dose is about 210 mg/kg per week. In one embodiment, the dose is about 220 mg/kg per week. In one embodiment, the dose is about 230 mg/kg per week. In one embodiment, the dose is about 240 mg/kg per week. In one embodiment, the dose is about 250 mg/kg per week. In one embodiment, the dose is about 260 mg/kg per week. In one embodiment, the dose is about 270 mg/kg per week. In one embodiment, the dose is about 280 mg/kg per week. In one embodiment, the dose is about 290 mg/kg per week. In one embodiment, the dose is about 300 mg/kg per week. In one embodiment, the dose is about 310 mg/kg per week. In one embodiment, the dose is about 320 mg/kg per week. In one embodiment, the dose is about 330 mg/kg per week. In one embodiment, the dose is about 340 mg/kg per week. In one embodiment, the dose is about 350 mg/kg per week.

In one aspect of the invention, administration of the modified NK cell composition and/or unbound anti-chemorepellant agent is pulsatile for a period of time sufficient to have an anti-chemorepellant effect (e.g., to attenuate the chemorepellant effect of the tumor cell). In one embodiment, an amount of modified NK cell composition and/or unbound anti-chemorepellant agent is administered every 1 hour to every 24 hours, for example every 1 hour, 2 hours, 3 hours, 4 hours, 5 hours, 6 hours, 7 hours, 8 hours, 9 hours, 10 hours, 11 hours, 12 hours, 13 hours, 14 hours 15 hours, 16 hours, 17 hours, 18 hours, 19 hours, 20 hours, 21 hours, 22 hours, 23 hours, or 24 hours. In one embodiment, an amount of modified NK cell composition and/or unbound anti-chemorepellant agent is administered every 1 day, 2 days, 3 days, 4 days, 5 days, 6 days, 7 days, 8 days, 9 days, or 10 days.

In one embodiment wherein the anti-chemorepellant agent is AMD3100, the dose of AMD3100 or a pharmaceutically acceptable salt thereof is between about 0.002 mg per kg body weight (mg/kg) and about 0.12 mg/kg per day. In one embodiment, the dose of AMD3100 or a pharmaceutically acceptable salt thereof is between about 0.002 mg/kg and about 0.10 mg/kg per day, between about 0.002 mg/kg and about 0.08 mg/kg per day, between about 0.002 mg/kg and about 0.06 mg/kg per day, or between about 0.002 mg/kg and about 0.04 mg/kg per day. In one embodiment, the dose of AMD3100 or a pharmaceutically acceptable salt thereof is between about 0.002 mg/kg and about 0.02 mg/kg per day. Contemplated values include any value, subrange, or range within any of the recited ranges, including endpoints.

In one aspect, AMD3100 is administered as a single bolus per day. In one embodiment, AMD3100 is administered once every one, two, three, four, five, six, seven, eight, nine, ten, eleven, or twelve days. In one embodiment, AMD3100 is administered via two, three, four or more sub-doses per day.

In one aspect, AMD3100 is administered via infusion or controlled release. In one embodiment, AMD3100 is administered over 1 to 24 hours. In one embodiment, the patient is administered AMD3100 for up to 1, 1, 2, 3, or 4 days.

In one aspect, AMD3100 is administered locally to a site of a tumor or near to the tumor. In one embodiment, AMD3100 is administered via a pump, continuous release, or other similar mechanism. In one embodiment, AMD3100 is administered by continuous infusion.

ADDITIONAL EMBODIMENTS

One aspect of the current invention relates to a method for making a modified NK cell composition having overall anti-chemorepellant properties, by contacting an NK cell population with an anti-chemorepellant agent to provide a modified NK cell population having anti-chemorepellant properties for the effective and efficient treatment of tumors or cancers. In one embodiment, the anti-chemorepellant agent is AMD3100.

One aspect of the current invention relates to a composition comprising modified NK cells and an anti-chemorepellant agent, wherein said composition has anti-chemorepellant properties for the effective and efficient treatment of tumors or cancers in a patient. In one embodiment, the anti-chemorepellant agent is AMD3100.

In one embodiment, the NK cells are modified as described herein. The NK cells may be genetically modified, for example by insertion of an exogenous gene (including but not limited to a gene expressing a cytokine, e.g., IL-2; CXCR7; CD16; or a CAR).

Anti-Cancer Vaccines

In an aspect of the present invention, modified NK cells are administered in combination with an anticancer vaccine (also called cancer vaccine). Anticancer vaccines are vaccines that either treat existing cancer or prevent development of a cancer by stimulating an immune reaction to attack the cancer cells. In one embodiment, the anticancer vaccine treats existing cancer.

The anticancer vaccine may be any such vaccine having a therapeutic effect on one or more types of cancer. Many anticancer vaccines are currently known in the art. Such vaccines include, without limitation, dasiprotimut-T, Sipuleucel-T, talimogene laherparepvec, HSPPC-96 complex (Vitespen), L-BLP25, gp100 melanoma vaccine, and any other vaccine that stimulates an immune response to cancer cells when administered to a patient.

Cancers

Cancers or tumors that can be treated by the compounds and methods described herein include, but are not limited to: anal cancer; biliary tract cancer; brain cancer, including glioblastomas and medulloblastomas; breast cancer, e.g., inflammatory breast cancer; cervical cancer; choriocarcinoma; colon cancer; endometrial cancer; esophageal cancer, gastric cancer; head and neck cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; mesothelioma; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors escaping immune recognition include glioma, anal cancer, colon carcinoma, colorectal cancer, head and neck cancer, lymphoid cell-derived leukemia, choriocarcinoma, ovarian cancer, melanoma, and mesothelioma. In some embodiments, the cancer is a human papilloma virus-positive cancer.

In one embodiment, the cancer is a solid tumor. In one embodiment, the cancer is a leukemia. In one embodiment, the cancer over-expresses CXCL12. In one embodiment, cancer expression of CXCL12 can be evaluated prior to administration of a composition as described herein. For example, a patient having a cancer that is determined to express or over-express CXCL12, e.g., a concentration of about 100 nM or higher, e.g., about 100, 150, 200, 250, 300, 350, 400, 450, or 500 nM, will be treated using a method and/or composition as described herein.

In one embodiment, the tumor is an anal cancer, head and neck cancer, gastric cancer, ovarian cancer, breast cancer, or mesothelioma. It is contemplated that an anal cancer, head and neck cancer, gastric cancer, ovarian cancer, breast cancer, or mesothelioma can be injected with a composition comprising the modified NK cells described herein. In one embodiment, an anticancer agent is administered directly to an anal cancer, head and neck cancer, gastric cancer, ovarian cancer, breast cancer, or mesothelioma via a catheter into a blood vessel within or proximal to the anal cancer, head and neck cancer, gastric cancer, ovarian cancer, breast cancer, or mesothelioma. Further discussion of catheter or microcatheter administration is described below.

In one aspect of this invention is provided a method for treating cancer in a patient in need thereof by administering modified NK cells. One of skill in the art will recognize that administering modified NK cells includes administering pharmaceutical compositions comprising the modified cells. In one embodiment, the modified NK cells are administered in combination with at least one additional anti-chemorepellant and/or anticancer agent.

The efficacy of a treatment as described herein for the treatment of a tumor can be determined by the skilled clinician. However, a treatment is considered "effective treatment," as the term is used herein, if any one or all of the signs or symptoms of the tumor, e.g., the growth, progression and/or metastasis of the tumor is inhibited, and/or other clinically accepted symptoms or markers of tumor are improved or ameliorated, e.g., by at least 10% following treatment with modified NK cells. Efficacy can also be measured by failure of an individual to worsen as assessed by hospitalization or need for medical interventions (e.g., progression of the tumor is halted or at least slowed). Methods of measuring these indicators are known to those of skill in the art and/or described herein.

One aspect of this invention is the inhibition of metastasis of a tumor in a patient in need thereof by administering modified NK cells to the patient with or without another conventional anticancer therapy. In an aspect of this invention, the modified NK cells of this invention may be administered to the patient in combination with an anti-chemorepellant agent. Without being bound by theory, it is believed that anti-chemorepellant agent can mobilize cancer cells out of niches where they are otherwise inaccessible and into the circulation where the tumor cells can also be targeted by other immune cells. Surprisingly, such mobilization does not lead to increased metastasis of the tumor, but rather decreases metastasis.

In an aspect of this invention a population of immune cells may be administered to a patient in need thereof wherein the population comprises the modified NK cells of this invention. The population of immune cells administered to a patient in need thereof comprising the modified NK cells of this invention, may further comprise, relative to the patient, autologous, allogeneic, or xenographic immune cells.

In one aspect, this invention relates to a method for killing a tumor cell expressing an amount of a chemokine, e.g., CXCL12, sufficient to produce a chemorepellant effect, which method comprises:

a) periodically contacting the tumor cell with an effective amount of modified NK cells, e.g., modified NK cells that (i) express CXCR7 and/or express a CAR, (ii) express no or substantially no CXCR4, or (iii) combinations of (i) and (ii), and an anti-chemorepellant agent composition for a sufficient period of time so as to attenuate said chemorepellant effect;

b) contacting the tumor cell with at least one additional anticancer agent; and c) optionally repeating a) and b) as necessary to kill the tumor cell.

In another aspect, this invention relates to a method for treating a tumor in a mammal, said tumor expressing an amount of a chemokine, e.g., CXCL12, sufficient to produce a chemorepellant effect, which method comprises:

a) periodically administering to a patient in need thereof an effective amount of modified NK cells, e.g., CAR-modified NK cells also expressing CXCR7 or also expressing no or substantially no CXCR4, and an anti-chemorepellant agent composition for a sufficient period of time so as to attenuate said chemorepellant effect;

b) administering to said mammal at least one additional anticancer agent; and c) optionally repeating a) and b) as necessary to provide an improvement in the condition of the mammal.

In one embodiment, the anticancer agent is administered after the period of time of administration of the CAR-modified NK cells, e.g., CAR-modified NK cells also expressing CXCR7 and/or also expressing no or substantially no CXCR4, and anti-chemorepellant agent. In an aspect of this invention, the anticancer agent is administered during a period of time when the chemorepellant effect is attenuated.

In another aspect of the invention, the cancer cell is a solid tumor cell. In one embodiment, the cancer cell is an anal cancer cell, a head and neck cancer cell, a breast cancer cell, an ovarian cancer cell, a gastric cancer cell, or a mesothelioma cell. In an embodiment, the breast cancer is inflammatory breast cancer. In the methods of this invention, the additional anticancer agent may be administered within about 3 days of completion of contacting the cell with a combination of the modified NK cells and anti-chemorepellant agent. The anticancer agent may be administered within about 1 day of completion of contacting the cell with the combination of CAR-modified NK cells, e.g., CAR-modified NK cells also expressing CXCR7 and/or also expressing no or substantially no CXCR4, and anti-chemorepellant agent.

This invention also relates to a method for treating a solid tumor in a patient, which tumor expresses CXCL12 at a concentration sufficient to produce a chemorepellant effect, the method comprising administering to the patient an effective amount of a composition comprising modified NK cells. The modified NK cells may be administered with an anticancer agent concurrently or sequentially. The modified NK cells may also be administered with an anti-chemorepellant agent for a sufficient period of time so as to inhibit said chemorepellant effect, followed by administering to said mammal at least one anticancer agent. In one embodiment, the cancer is an anal cancer, a head and neck cancer, an ovarian cancer, a gastric cancer, a breast cancer, e.g., inflammatory breast cancer, or a mesothelioma. The anticancer agent may be administered within about 3 days of completion of administration of the modified NK cells or within about 3 days of completion of administration of the modified NK cells and/or the anti-chemorepellant agent. The anticancer agent may be administered within about 1 day of completion of administration of the modified NK cells. The anticancer agent may be administered within about 1 day of completion of administration of the modified NK cells and/or the anti-chemorepellant agent.

In one aspect, this invention relates to the treatment of a patient having a solid tumor expressing a chemokine, e.g., CXCL12, by contacting the tumor with a pharmaceutical composition comprising the modified NK cells described herein and a chemotherapeutic agent. In one embodiment, the tumor is a solid tumor, e.g., an anal cancer, a head and neck cancer, an ovarian cancer, a gastric cancer, a breast cancer, e.g., inflammatory breast cancer, or a mesothelioma.

In one aspect, this invention relates to a method of locally treating a solid tumor expressing CXCL12 at a concentration sufficient to produce a chemorepellant effect in a patient, which method comprises:
a) identifying an artery or microartery feeding said tumor;
b) intra-arterially placing a catheter or microcatheter in said artery or microartery proximal to the flow of blood into said tumor wherein said catheter or microcatheter comprises a lumen for delivering a fluid there through and means for delivering said fluid;
c) periodically administering an effective amount of the modified NK cells through said catheter or said microcatheter to the artery or microartery feeding said tumor so as to inhibit the growth, progression and/or metastasis of the tumor; and
d) subsequently administering an effective amount of an anticancer agent to the patient.

The method may further comprise repeating steps a, b, c, and/or d until the patient's condition improves. In one embodiment, the method further comprises administering an anticancer agent to the patient. The anticancer agent may be administered via a catheter, a microcatheter, an external radiation source, or is injected or implanted proximal to or within the tumor. The anticancer agent may be a radiotherapeutic agent, such that the radiotherapeutic agent causes ablation of at least one blood vessel feeding said tumor. The tumor may be an anal cancer, a head and neck cancer, an ovarian cancer, a gastric cancer, a breast cancer, e.g., inflammatory breast cancer, or a mesothelioma.

The foregoing is illustrative of the present invention, and is not to be construed as limiting thereof. The invention is defined by the following claims, with equivalents of the claims to be included therein.

What is claimed is:
1. An ex vivo modified NK cell that has been modified to express:
   (a) CXCR7 on the surface of the cell, or
   (b) CXCR7 on the surface of the cell and no or substantially no CXCR4 receptors on the surface of the cell.
2. The ex vivo modified NK cell of claim 1, wherein the NK cell is a NK-92 cell, a NKYS cell, a KHYG-1 cell, a NKL cell, a NKG cell, a SNK-6 cell, or an IMC-1 cell.
3. The ex vivo modified NK cell of claim 1, wherein the modified NK cell is further modified to express a tumor cell homing receptor on the surface of the modified cell.
4. The ex vivo modified NK cell of claim 3, wherein the tumor cell homing receptor is a chimeric antigen receptor (CAR), an Fc receptor, or combinations thereof.
5. The ex vivo modified NK cell of claim 4, wherein the CAR targets a cancer-associated antigen.
6. The ex vivo modified NK cell of claim 5, wherein the cancer-associated antigen is selected from the group consisting of folate receptor-α, CAIX, CD19, CD20, CD30, CD33, CEA, EGP-2, erb-B2, erb-B 2,3,4, FBP, GD2, GD3, Her2/neu, IL-13R-a2, k-light chain, LeY, MAGE-A1, mesothelin, and PSMA.
7. The ex vivo modified NK cell of claim 3, wherein the modified NK cell expresses an endogenous tumor cell homing receptor that is not CXCR4.
8. The ex vivo modified NK cell of claim 1, wherein the NK cells are NK-92 cells genetically modified to express a CD-16 receptor or interleukin-2 (IL-2).
9. An ex vivo cell population comprising:
   (a) a modified NK cell that has been modified to express CXCR7 on the surface of the modified cell, or
   (b) a modified NK cell that has been modified to have no or substantially no CXCR4 receptors on the surface of the cell and to express CXCR7 on the surface of the modified cell, or
   (c) combinations of the modified NK cells of (a) and (b).
10. The cell population of claim 9, wherein the NK cell is a NK-92 cell, a NK-YS cell, a KHYG-1 cell, a NKL cell, a NKG cell, a SNK-6 cell, or an IMC-1 cell.
11. The cell population of claim 9, wherein the modified NK cell is further modified to express a tumor cell homing receptor on the surface of the modified cell.
12. The cell population of claim 11, wherein the tumor cell homing receptor is a CAR, an Fc receptor, or combinations thereof.
13. The cell population of claim 12, wherein the CAR targets a cancer-associated antigen.
14. The cell population of claim 13, wherein the cancer-associated antigen is selected from the group consisting of folate receptor-α, CAIX, CD19, CD20, CD30, CD33, CEA, EGP54 2, erb-B2, erb-B 2,3,4, FBP, GD2, GD3, Her2/neu, IL-13R-a2, k-light chain, LeY, MAGE-A1, mesothelin, and PSMA.
15. The cell population of claim 9, wherein the NK cells are NK-92 cells genetically modified to express a CD-16 receptor or interleukin-1 (IL-2).
16. A pharmaceutical composition comprising an effective amount of the modified NK cells of claim 1 and one or more pharmaceutically acceptable excipients.
17. A method for treating a patient having a tumor which expresses CXCL12, wherein said patient is administered an effective amount of the modified NK cells of claim 1.
18. A method for making a modified NK cell composition having overall anti-chemorepellant properties, comprising contacting the cell population of claim 9 with an anti-chemorepellant agent to provide a cell population having anti-chemorepellant properties for the treatment of tumors or cancers.
19. A method for making an NK cell composition having overall anti-chemorepellant properties, comprising contacting the modified NK cell of claim 1 with an anti-chemorepellant agent ex vivo to provide an NK cell population having anti-chemorepellant properties for the treatment of tumors or cancers.

20. A method for treating a patient having a cancer which expresses CXCL12, comprising administering to the patient an effective amount of the modified NK cells of claim 1 contacted ex vivo with an amount of an anti-chemorepellant agent sufficient to enhance the migration of the cells to the cancer.

* * * * *